United States Patent
McGill et al.

(10) Patent No.: US 7,524,103 B2
(45) Date of Patent: Apr. 28, 2009

(54) APPARATUS FOR MIXING AND DISPENSING A MULTI-COMPONENT BONE CEMENT

(75) Inventors: Scott McGill, San Ramon, CA (US); Mukund R. Patel, San Jose, CA (US); Harold F. Carrison, Pleasanton, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 573 days.

(21) Appl. No.: 10/922,746

(22) Filed: Aug. 19, 2004

(65) Prior Publication Data

US 2005/0105385 A1     May 19, 2005

Related U.S. Application Data

(63) Continuation-in-part of application No. 10/716,641, filed on Nov. 18, 2003, now abandoned.

(51) Int. Cl.
*B01F 7/00* (2006.01)
*B01F 15/02* (2006.01)
*B01F 3/14* (2006.01)

(52) U.S. Cl. .............. 366/189; 366/192; 366/195; 366/289; 366/332

(58) Field of Classification Search ............ 366/139, 366/189, 332, 333, 194, 195, 196, 192, 289, 366/255, 256, 182.3, 182.4; 604/185, 187
See application file for complete search history.

(56) References Cited

U.S. PATENT DOCUMENTS

| | | | | |
|---|---|---|---|---|
| 1,458,282 A * | 6/1923 | Fairbanks | .................. | 366/289 |
| 1,998,692 A * | 4/1935 | Rossem et al. | .............. | 366/333 |
| 2,825,134 A * | 3/1958 | Hicks | ........................ | 433/90 |
| 3,140,078 A * | 7/1964 | Krahe et al. | ................. | 366/256 |
| 3,164,303 A * | 1/1965 | Trautmann | .................. | 222/190 |
| 3,188,057 A * | 6/1965 | Trumbull | .................... | 366/289 |
| 3,195,778 A * | 7/1965 | Coates | ........................ | 222/80 |
| 3,417,971 A * | 12/1968 | Blank et al. | ................. | 366/196 |
| 3,475,010 A * | 10/1969 | Cook et al. | ................. | 366/333 |
| 3,752,364 A * | 8/1973 | DeVries | ..................... | 222/131 |

(Continued)

FOREIGN PATENT DOCUMENTS

EP      0 397 589      11/1990

(Continued)

OTHER PUBLICATIONS

PCT Partial International Search Report for PCT/US2004/038499, Applicant: Scimed Life Systems, Inc., Form PCT/ISA/206, dated Mar. 22, 2005 (7 pages).

(Continued)

*Primary Examiner*—Tony G Soohoo
(74) *Attorney, Agent, or Firm*—Vista IP Law Group, LLP

(57) ABSTRACT

An apparatus for mixing and dispensing a multi-component compound. The device includes a tubular body with an internal chamber for mixing the multi-component compound. Disposed within and extending beyond the tubular body is a rod having a mixing disc located near a distal end. Also disposed within the tubular body is a moveable piston with a central opening through which the rod may pass.

8 Claims, 13 Drawing Sheets

U.S. PATENT DOCUMENTS

| | | | |
|---|---|---|---|
| 3,858,853 A * | 1/1975 | Rausch et al. | 366/279 |
| 4,132,361 A | 1/1979 | Ryd | |
| 4,277,184 A | 7/1981 | Solomon et al. | |
| 4,371,094 A * | 2/1983 | Hutter, III | 222/1 |
| 4,469,153 A * | 9/1984 | Morrisette | 141/364 |
| 4,671,263 A | 6/1987 | Draenert | |
| 4,676,655 A * | 6/1987 | Handler | 366/130 |
| 4,799,801 A * | 1/1989 | Bruning | 366/255 |
| 4,889,432 A * | 12/1989 | Patterson | 366/139 |
| 4,952,065 A * | 8/1990 | Kreuziger | 366/139 |
| 4,966,468 A * | 10/1990 | Bruning | 366/333 |
| 4,969,888 A | 11/1990 | Scholten et al. | |
| 4,973,334 A | 11/1990 | Ziemann | |
| 5,071,040 A * | 12/1991 | Laptewicz, Jr. | 222/235 |
| 5,108,404 A | 4/1992 | Scholten et al. | |
| 5,143,211 A * | 9/1992 | Miczka et al. | 206/221 |
| 5,193,907 A | 3/1993 | Faccioli et al. | |
| 5,252,301 A | 10/1993 | Nilson et al. | |
| 5,273,190 A * | 12/1993 | Lund | 222/83 |
| 5,398,483 A | 3/1995 | Smith et al. | |
| 5,435,645 A | 7/1995 | Faccioli et al. | |
| 5,478,342 A | 12/1995 | Kohrs | |
| 5,494,349 A | 2/1996 | Seddon | |
| 5,531,519 A | 7/1996 | Earle | |
| 5,588,136 A | 12/1996 | Watanabe | |
| 5,588,745 A | 12/1996 | Tanaka et al. | |
| 5,624,184 A | 4/1997 | Chan | |
| 5,676,666 A | 10/1997 | Oxland et al. | |
| 5,797,678 A | 8/1998 | Murray | |
| 5,797,679 A | 8/1998 | Grulke et al. | |
| 5,827,289 A | 10/1998 | Reiley et al. | |
| 5,842,785 A | 12/1998 | Brown et al. | |
| 5,842,786 A | 12/1998 | Solomon | |
| 5,865,847 A | 2/1999 | Kohrs et al. | |
| 5,876,116 A | 3/1999 | Barker et al. | |
| 5,897,593 A | 4/1999 | Kohrs et al. | |
| 5,951,160 A | 9/1999 | Ronk | |
| 5,961,211 A | 10/1999 | Barker et al. | |
| 5,972,015 A | 10/1999 | Scribner et al. | |
| 6,024,480 A | 2/2000 | Seaton et al. | |
| 6,033,105 A | 3/2000 | Barker et al. | |
| 6,042,262 A | 3/2000 | Hajianpour | |
| 6,059,790 A | 5/2000 | Sand et al. | |
| 6,066,154 A | 5/2000 | Reiley et al. | |
| 6,079,868 A | 6/2000 | Rydell | |
| 6,113,602 A | 9/2000 | Sand | |
| 6,116,773 A | 9/2000 | Murray | |
| 6,120,174 A | 9/2000 | Hoag et al. | |
| 6,120,506 A | 9/2000 | Kohrs et al. | |
| 6,165,219 A | 12/2000 | Kohrs et al. | |
| 6,176,607 B1 | 1/2001 | Hajianpour | |
| D439,980 S | 4/2001 | Reiley et al. | |
| 6,210,031 B1 | 4/2001 | Murray | |
| 6,235,043 B1 | 5/2001 | Reiley et al. | |
| 6,238,399 B1 | 5/2001 | Heller et al. | |
| 6,254,268 B1 | 7/2001 | Long | |
| 6,280,456 B1 | 8/2001 | Scribner et al. | |
| 6,286,670 B1 | 9/2001 | Smith | |
| 6,293,693 B1 * | 9/2001 | Rodgers et al. | 366/189 |
| D449,691 S | 10/2001 | Reiley et al. | |
| 6,296,149 B1 | 10/2001 | Long | |
| 6,348,055 B1 | 2/2002 | Preissman | |
| 6,361,539 B1 | 3/2002 | Heller et al. | |
| 6,367,962 B1 * | 4/2002 | Mizutani et al. | 366/189 |
| 6,395,006 B1 | 5/2002 | Burchett | |
| 6,406,175 B1 | 6/2002 | Marino | |
| 6,423,083 B2 | 7/2002 | Reiley et al. | |
| 6,425,897 B2 | 7/2002 | Overes et al. | |
| 6,431,743 B1 * | 8/2002 | Mizutani et al. | 366/189 |
| 6,435,705 B1 | 8/2002 | Long | |
| 6,439,439 B1 | 8/2002 | Rickard et al. | |
| 6,440,138 B1 | 8/2002 | Reiley et al. | |
| 6,458,136 B1 | 10/2002 | Allard et al. | |
| 6,468,279 B1 | 10/2002 | Reo | |
| D467,657 S | 12/2002 | Scribner | |
| 6,488,651 B1 * | 12/2002 | Morris et al. | 604/89 |
| 6,502,608 B1 | 1/2003 | Burchett et al. | |
| D469,871 S | 2/2003 | Sand | |
| D472,323 S | 3/2003 | Sand | |
| 6,536,937 B1 | 3/2003 | Burchett | |
| 6,547,432 B2 | 4/2003 | Coffeen et al. | |
| 6,550,957 B2 * | 4/2003 | Mizutani et al. | 366/189 |
| 6,572,256 B2 | 6/2003 | Seaton et al. | |
| 6,575,919 B1 | 6/2003 | Reiley et al. | |
| 6,582,439 B1 | 6/2003 | Sproul | |
| 6,592,247 B1 | 7/2003 | Brown et al. | |
| 6,592,251 B2 | 7/2003 | Edwards et al. | |
| 6,599,293 B2 | 7/2003 | Tague | |
| 6,607,544 B1 | 8/2003 | Boucher et al. | |
| 6,610,091 B1 | 8/2003 | Reiley | |
| 6,613,054 B2 | 9/2003 | Scribner et al. | |
| 6,623,505 B2 | 9/2003 | Scribner et al. | |
| 6,626,912 B2 | 9/2003 | Speitling | |
| D482,787 S | 11/2003 | Reiss | |
| 6,641,587 B2 | 11/2003 | Scribner et al. | |
| 6,648,499 B2 * | 11/2003 | Jonsson | 366/139 |
| D483,495 S | 12/2003 | Sand | |
| 6,655,828 B2 | 12/2003 | Vendrely et al. | |
| 6,663,647 B2 | 12/2003 | Reiley et al. | |
| 6,663,669 B1 | 12/2003 | Reiley | |
| 6,673,116 B2 | 1/2004 | Reiley | |
| 6,702,455 B2 | 3/2004 | Vendrely | |
| 6,709,149 B1 | 3/2004 | Tepic | |
| 6,719,761 B1 | 4/2004 | Reiley et al. | |
| D490,159 S | 5/2004 | Sand | |
| 6,736,537 B2 * | 5/2004 | Coffeen et al. | 366/130 |
| 6,910,799 B2 * | 6/2005 | Renfro | 366/169.1 |
| 6,974,247 B2 * | 12/2005 | Frei et al. | 366/255 |
| 2001/0011174 A1 | 8/2001 | Reiley et al. | |
| 2002/0013553 A1 | 1/2002 | Pajunk et al. | |
| 2002/0013600 A1 | 1/2002 | Scribner et al. | |
| 2002/0026195 A1 | 2/2002 | Layne et al. | |
| 2002/0082608 A1 | 6/2002 | Reiley et al. | |
| 2002/0099385 A1 | 7/2002 | Ralph et al. | |
| 2002/0156482 A1 | 10/2002 | Scribner et al. | |
| 2002/0156483 A1 | 10/2002 | Voellmicke et al. | |
| 2002/0161373 A1 | 10/2002 | Osorio et al. | |
| 2002/0169471 A1 | 11/2002 | Ferdinand | |
| 2002/0183778 A1 | 12/2002 | Reiley et al. | |
| 2002/0188299 A1 | 12/2002 | Reiley et al. | |
| 2003/0004530 A1 | 1/2003 | Reo et al. | |
| 2003/0012079 A1 | 1/2003 | Coffen et al. | |
| 2003/0012080 A1 | 1/2003 | Coffeen et al. | |
| 2003/0014056 A1 | 1/2003 | Tague et al. | |
| 2003/0032963 A1 | 2/2003 | Reiss et al. | |
| 2003/0032964 A1 | 2/2003 | Watkins et al. | |
| 2003/0075564 A1 | 4/2003 | Wahlig et al. | |
| 2003/0109884 A1 | 6/2003 | Tague et al. | |
| 2003/0130664 A1 | 7/2003 | Boucher et al. | |
| 2003/0191414 A1 | 10/2003 | Reiley et al. | |
| 2003/0191489 A1 | 10/2003 | Reiley et al. | |
| 2003/0195547 A1 | 10/2003 | Scribner et al. | |
| 2003/0220648 A1 | 11/2003 | Osorio et al. | |
| 2003/0229372 A1 | 12/2003 | Reiley et al. | |
| 2004/0030345 A1 | 2/2004 | Aurin et al. | |
| 2005/0111299 A1 * | 5/2005 | Frei et al. | 366/255 |
| 2006/0052794 A1 | 3/2006 | McGill et al. | |

FOREIGN PATENT DOCUMENTS

| | | |
|---|---|---|
| EP | 0 445 951 | 9/1991 |
| EP | 1 0901 609 | 4/2001 |

| | | |
|---|---|---|
| GB | 2 338 428 | 12/1999 |

OTHER PUBLICATIONS

PCT International Search Report for PCT/US2004/038499, Applicant: Scimed Life Systems, Inc., Forms PCT/ISA/210 and 220, dated Jun. 2, 2005 (10 pages).

PCT Written Opinion of the International Search Authority for PCT/US2004/038499, Applicant: Scimed Life Systems, Inc., Form PCT/ISA/237, dated Jun. 2, 2005 (9 pages).

Non-Final Office Action dated Dec. 28, 2006 for related U.S. Appl. No. 10/956,249, filed Sep. 30, 2004, Inventor Scott McGill (11 pages).

* cited by examiner

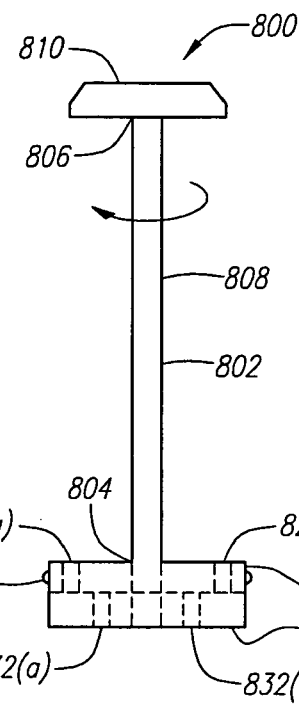
FIG. 8A
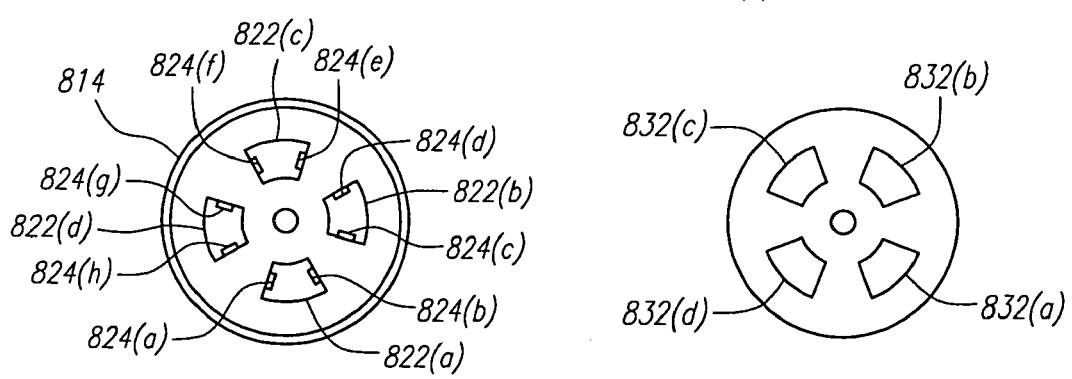
FIG. 8B    FIG. 8C
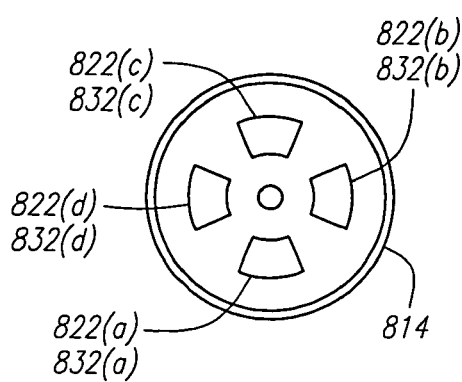 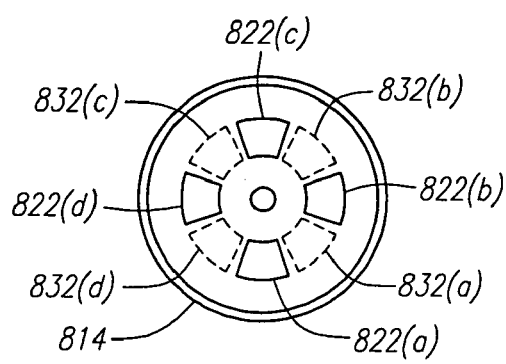
FIG. 8D    FIG. 8E

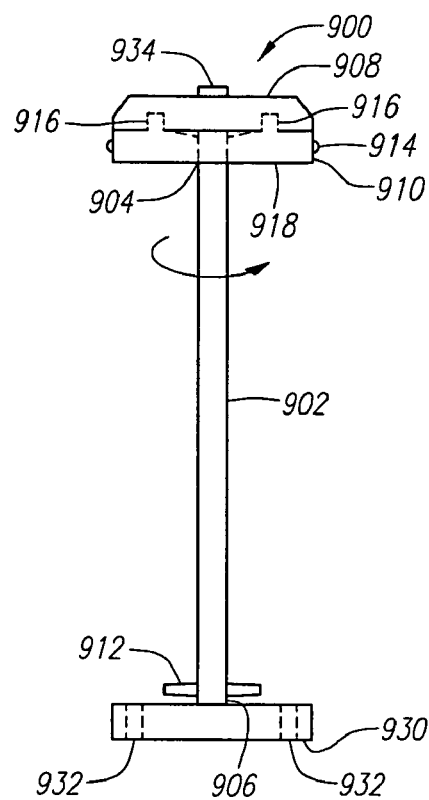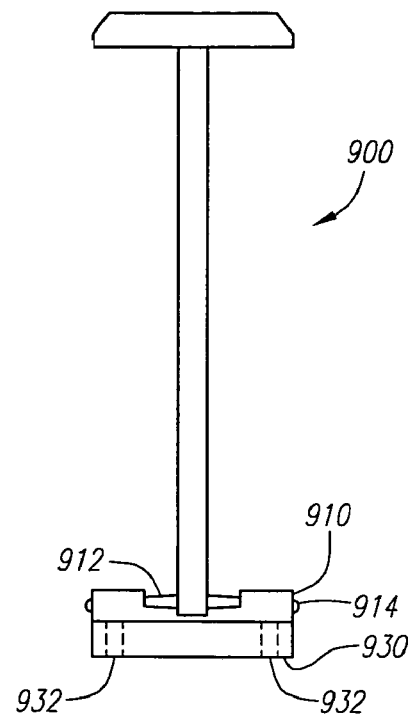
FIG. 9A　　　　FIG. 9B
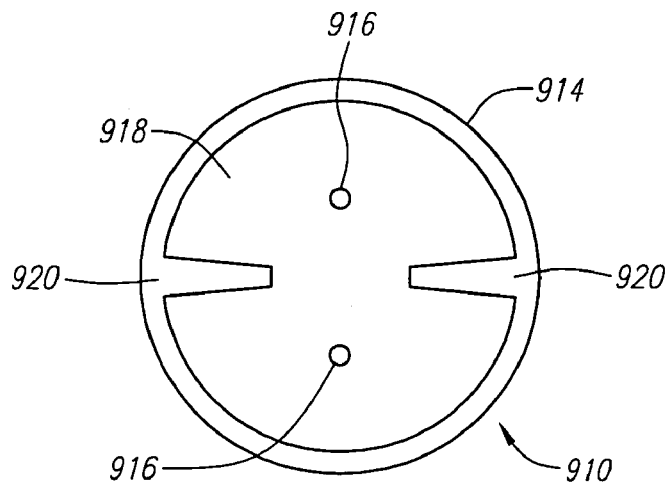
FIG. 9C

APPARATUS FOR MIXING AND DISPENSING A MULTI-COMPONENT BONE CEMENT

RELATED APPLICATION DATA

This application is a continuation-in-part of U.S. patent application Ser. No. 10/716,641 filed Nov. 18, 2003, now abandoned, the disclosure of which is fully incorporated by reference herein.

BACKGROUND OF THE INVENTION

1. Field of the Invention

The present invention pertains to methods and apparatus for mixing and dispensing a multi-component cement, such as bone cement, for injection into a body.

2. Background of the Invention

Joints and bones in the human body are often subject to degeneration as a result of disease or trauma. One way of treating this degeneration is to replace the joints or bones using artificial materials. Bone cements play a critical role in this process by acting to anchor implants into place or otherwise help in restructuring degenerated joints and bones.

Bone cements are usually comprised of a liquid monomer component that polymerizes about a polymeric powder component. Typically, the liquid monomer and powdered polymer are mixed just prior to using the bone cement because the mixed cement tends to cure rapidly. During the mixing process, the liquid monomer and powdered polymer react exothermically (i.e., producing heat) and create malodorous vapors. It is desirable for the user to minimize exposure to the vapors and also to ensure that the cement is thoroughly mixed and able to be delivered quickly. In addition, precise control of the cement flow from the device is highly desirable, as it is critical to inject the proper amount of cement, and to make the injection when the cement has the proper consistency.

Various devices have been presented for the mixing and dispensing of bone cement. By way of example, U.S. Pat. No. 6,033,105 discloses an open-ended system where the cement ingredients are mixed in a container using hand-turned mixing blades. After mixing, the cement is delivered to a body location by activation of a corkscrew device that is part of the mixing mechanism. U.S. Pat. No. 6,079,868 teaches mixing and delivery of two ingredients by extruding the ingredients through a static mixing chamber. U.S. Pat. No. 6,286,670 discloses a single vessel for storing a liquid monomer and a solid polymer isolated by a barrier, which may be removed or broken for combining the ingredients to form the cement. U.S. Pat. No. 6,406,175 discloses a mixing and delivery device that is pre-packed with a polymer powder, wherein a user injects the liquid monomer into the device just prior to use. The above-referenced patents are incorporated herein for all that they teach and disclose.

SUMMARY OF THE INVENTION

The invention is directed to apparatus and methods for mixing and delivering compounds into a body, and more particularly to apparatus and methods for delivering bone cement, biomaterials, and/or other flowable compounds In one embodiment, the apparatus includes a tubular body defining an internal chamber for mixing the multi-component compound. The tubular body has a distal end with an opening in communication with the internal chamber. A rod disposed within the tubular body, the rod has a mixing disc located near the distal end of the rod. In addition, a moveable piston that is separate from the tubular body is contained within the tubular body The piston may be configured such that it has an opening through which the rod may be disposed.

The proximal end of the tubular body may be configured with a removable cover. The moveable piston may be attached to the removable cover.

The apparatus may also be configured so that the moveable piston may be attached or secured adjacent to the mixing disc at the distal end of the rod.

In one embodiment, the apparatus includes a rod with a distal end and a proximal end. The rod has a handle located at its proximal end. The rod also has a first mixing disc and a second mixing disc located near its distal end.

The first mixing disc may have multiple perforations. The second mixing disc may also have multiple perforations. The first mixing disc may be configured with clips designed to join the first mixing disc to the second mixing disc. When joined the first mixing disc and the second mixing disc create a piston mechanism. The first mixing disc and the second mixing disc may have the same number of perforations.

In one embodiment the apparatus includes a rod with a distal end and a proximal end. A handle is located at the proximal end of the rod and a mixing disc is located near the distal end of the rod. The apparatus also has a moveable piston.

The moveable piston may be configured with an opening, through which the rod may be disposed. In addition the moveable piston may have a sealing means about its periphery; for example, the moveable piston may have an o-ring or gasket about its periphery. The moveable piston may also be configured to be removably attached to the handle at the proximal end of the rod. The engaging or release of the moveable piston to the handle may be performed through a push button mechanism.

The mixing disc may have multiple perforations.

On embodiment of the invention is a valve that is a sliding apparatus. The valve includes a moveable part to control fluid communication. There is an arm connected to the moveable part and a button to engage the arm for displacing the moveable part.

The moveable part may be a flat member. The moveable part is designed to control fluid communication between two chambers. For example one of the chambers may be a mixing chamber and the other may be a delivery chamber. The two chambers may be substantially perpendicular to one another. The moveable part may translate along the axial length of the delivery chamber or it may translate across the axial length of the delivery chamber.

In accordance with another aspect of the invention, a method is provided for mixing and delivering a flowable compound, e.g., bone cement. The mixing rod including a mixing disc at the distal end is inserted in a tubular device and the tubular device is filled with a multi-component flowable compound. The mixing rod is then axially displaced within the tubular device to mix the flowable compound. After the flowable compound is mixed, a moveable piston located near the distal end of the mixing rod is engaged to dispense the flowable compound from the tubular device.

The moveable piston may be engaged by pulling the mixing rod to the proximal end of the tubular device where the moveable piston is located. Then the mixing rod is rotated about its axial length to engage the moveable piston.

Alternatively, the moveable piston may be engaged by pulling the mixing rod to a proximal end of the tubular device where the moveable piston is located and then locking the moveable piston to the mixing disc by mechanical means.

Other objects and features of the invention will become apparent from consideration of the following description taken in conjunction with the accompanying drawings.

BRIEF DESCRIPTION OF THE DRAWINGS

The drawings illustrate the design and utility of preferred embodiments of the invention, in which similar elements are referred to by common reference numerals, and in which:

FIG. 8A is a cut-away elevated side view of a bone cement mixing/dispensing rod according to a further aspect of the invention.

FIGS. 8B-8E are plan views of one embodiment of mixing/dispensing discs for use with the mixing/dispensing rod of FIG. 8A.

FIGS. 9A and 9B are cut-away elevated side views of a bone cement mixing/dispensing rod according to yet another aspect of the invention.

FIG. 9C is a plan view of one embodiment of an ejection piston for use with the mixing/dispensing rod of FIGS. 9A-9B.

DETAILED DESCRIPTION OF THE ILLUSTRATED EMBODIMENTS

Figure 1A:
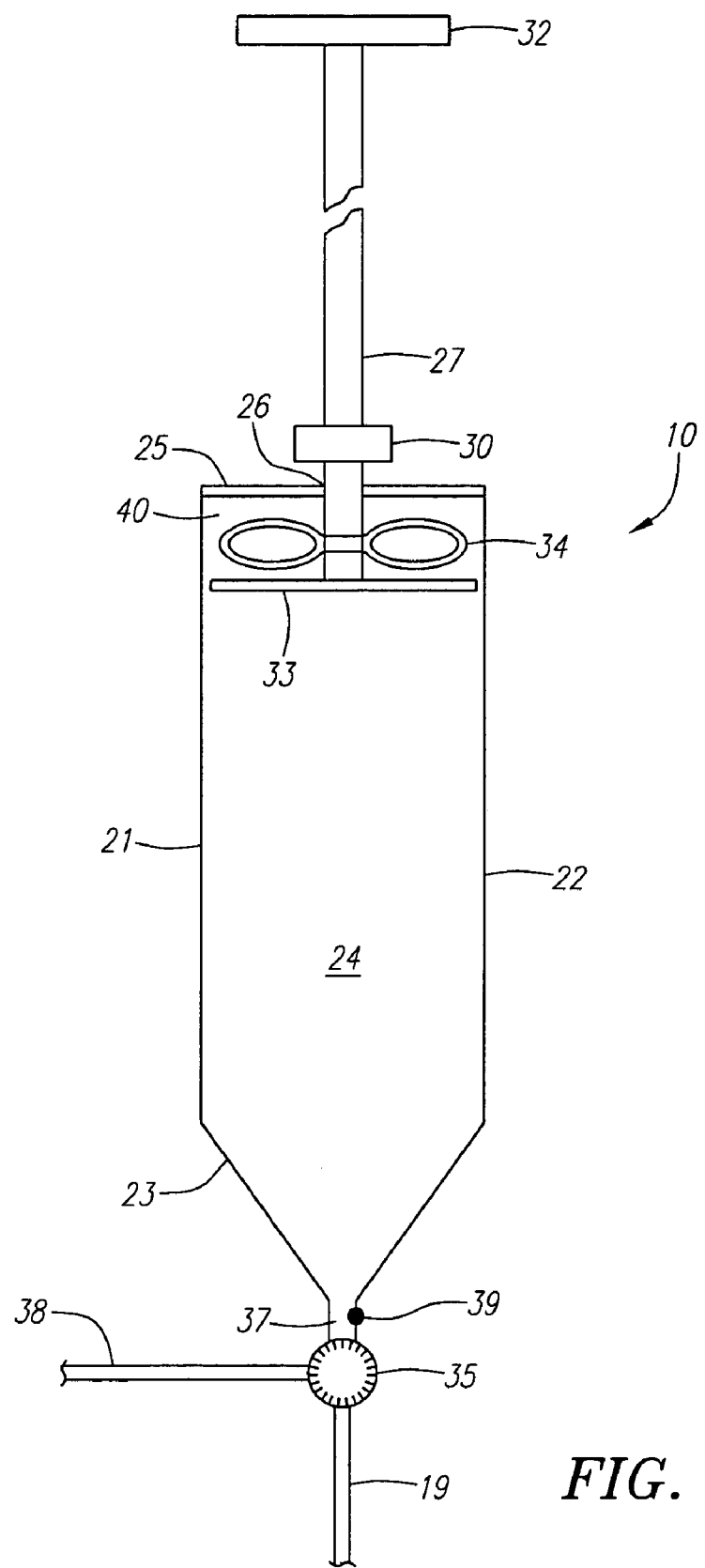
FIGS. 1A and 1B are cut-away, elevated side views of a first embodiment of a bone cement mixing/dispensing device, according to one aspect of the invention.

Various embodiments of the present invention are described hereinafter with reference to the figures. It should be noted that the figures are not drawn to scale and that elements of similar structures or functions are represented by like reference numerals throughout the figures. It should also be noted that the figures are only intended to facilitate the description of specific embodiments of the invention, and are not intended as an exhaustive description, or as a limitation on the scope, of the invention. Aspects, features, and advantages described in conjunction with a particular embodiment are not necessarily limited to that embodiment and may be practiced with other embodiments of the invention, even if not so illustrated or specifically described.

Further, while the inventive concepts and devices are shown and described herein for the purpose of mixing and dispensing of bone cements, such as PMMA bone cements, other types of biomaterials, e.g., ceramics, such as calcium aluminate, calcium, phosphate, calcium sulfate, etc., can also be mixed and dispensed by the apparatus of the invention.

Figure 1B:
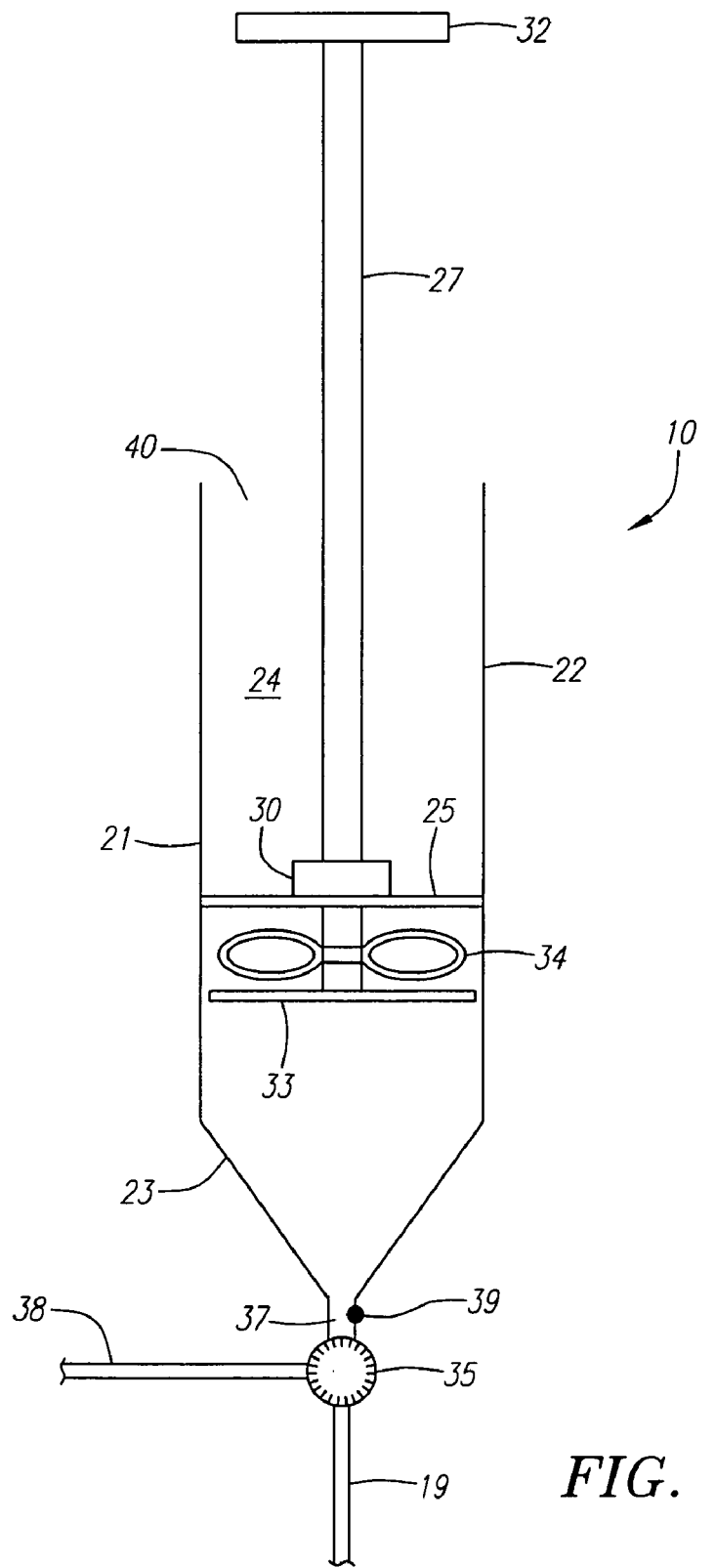

FIGS. 1A and 1B depict a device 10 for mixing and dispensing bone cement to a cannula (not shown) inserted in a selected body (i.e., bone) cavity (also not shown). The device 10 includes a tubular body 21 having a proximal portion 22 and a tapered distal portion 23, and forming an internal mixing chamber 24. The tapered distal portion 23 has a narrow opening 37 in communication with the mixing chamber 24. The tubular body 21 also has a proximal opening 40, sealed by a movable ejection piston 25. In particular, the ejection piston 25 has an outer circumference sized to snuggly fit in the inner circumference of the tubular body 21. A gasket, or other type of sealing means (not shown) may be disposed about the periphery of the piston 25 to prevent the cement contents in the chamber 24 from passing between the piston 25 and internal wall of the tubular body 21. In an alternate embodiment, a separate (preferably removable) cover may be provided to seal the proximal opening 40 and the chamber 24 separate from the ejection piston 25.

The piston 25 has a central opening 26 through which a rod 27 extends into the chamber 24. A handle 32 is attached to the proximal end of the rod 27. Again, a gasket or other sealing means (not shown) is provided around the circumference of opening 26, such that the rod 27 moves slidably there through, in order to provide a seal between the chamber 24 and the external atmosphere. Preferably, the rod 27 fits snuggly through the opening 26, but is movable relative to the tubular body 21 without a user having to exert undue force. In alternate embodiments, the rod 27 may be fixed to the piston 25, or a latch mechanism (not shown) may be employed to allow the user to selectively fix the rod 27 to the piston 25.

In the illustrated embodiment, a stop ring 30 is selectively placed around the rod 27 to limit the distance that the rod 27 may be extended into the chamber 24. Preferably, a user of the device 10 may fix the stop ring 30 at a desired position along the length of the rod 27, although it may also be fixed to begin with. By way of non-limiting example, the stop ring 30 may be compliant and snuggly, but movably, stretched around the rod 27. Alternately, the stop ring 30 may be fixed to the rod 27 using a locking screw. As is illustrated in FIG. 1B, as the rod 27 is moved relative to the tubular body 21 and into the chamber 24, the stop ring 30 engages the piston 25, causing the piston 25 to be moved into the chamber 24 along with the rod 27.

In accordance with a main aspect of the invention, a perforated mixing disc 33 is attached to the distal end of the rod 27. As the disc 33 is moved through the chamber 24, the contents in the chamber 24 are passed through the perforations (not shown) in the disc 33 and mixed. As will be appreciated by those skilled in the art, the size of the perforations in the disc 33 may vary, and should be selected based on achieving the proper balance between being small enough to adequately mix the contents in the chamber 24, while being large enough to allow forward movement of the piston 25 without undue exertion on the part of the user, and without causing the seals around the respective perimeters of the piston 25 and rod 27 to fail. As will also be further appreciated, for the same reasons, the outer circumference of the mixing disc 33 may be varied, such that the disc 33 extends radially for up to all of the inner diameter of the proximal portion of the tubular body 21. It may be desirable in embodiments of the invention to add one or more static mixing elements, e.g., in the mixing chamber and/or in the delivery tubing (discussed below).

In the illustrated embodiment, a mixing impeller 34 is rotatably attached to the rod 27 between the ejection piston 25 and the mixing disc 33 to further facilitate mixing of the contents of the chamber 24. By way of non-limiting example, the impeller may comprise a plurality of angled mixing blades attached to a rotating collar on the rod 27, so that the blades are rotated around the rod 27 by force of the contents of the chamber 24 against the blades, as the impeller 34 is moved through the chamber 24. It will be appreciated that alternate embodiments of the invention may be provided with only one of the perforated mixing disc 33 and impeller 34.

A directing valve 35 is located at the distal opening 37 on the tubular body 21. In the illustrated device 10, the valve 35 is a three-way valve, which seals off the opening 37 in a first position; directs cement product extruded from the chamber 24 to a patient delivery tube 19 in a second position; and diverts the cement product extruded from the chamber 24 to a shunt relief tube 38 in a third position. The valve 35 may be manually or automatically controlled. An automatically controlled valve 35 may be controlled by any number of means, including a mechanical, hydraulic or electrical means. For example, the valve 35 may be controlled by an automatic means such that when the ejection disc 25 starts or stops moving in the lumen 24, the valve 35 is activated. While the respective shunt and delivery tubes 38 and 19 may be removably attachable to the distal opening 37, in one embodiment of the invention, the delivery tube 19 is permanently fixed to the tubular body 22, in at least one embodiment, the delivery tube 19 is permanently fixed to the body 22. For example, the body 22 and delivery tube 19 may be constructed using a single body injection mold, or other known manufacturing process. Alternately, they may be attached using a plastic welding process or adhesive bonding element.

In the illustrated device 10, a sensor 39 is provided proximal the cement extrusion opening 37, and may be used to control the valve 35 based on properties of the cement product in the chamber 24. For example, the sensor 39 could be a pressure gage that could tell the user when the compound in the chamber 24 is at a desired functional viscosity for patient delivery, in which case the valve 35 is moved to the second position to direct the cement into the patient tube 19; or if the viscosity is too great—i.e., signaling the cement has hardened beyond the point of safe delivery to the patient, in which case the valve 35 is moved to the third position to divert the cement into the shunt tube 38. By way of another, non-limiting, example, the sensor 39 could measure the temperature of the cement mixture in the chamber and, based on the known exothermic nature of the cement mixture, control the valve 35 for delivery to either the patient tube 19 or shunt tube 38, according to the temperature of the cement. In selected embodiments (not illustrated), feedback (readout) from the sensor may be an analogue or digital (e.g., numerical) display, a light indicator, a bar graph, or other visual display means. Alternately or additionally, the sensor output may be audible or vibrational.

In addition to relieving internal pressures when the plunger mechanism stops applying force, the shunt relief line 38 can also be designed to divert flow (and relieve pressure) at a maximum allowable pressure in the chamber 24. For example, the valve 35 may be automatically actuated to divert the cement flow to the shunt relief 38 at a given pressure in chamber 24 in order to prevent device failure, i.e. where the device breaks due to the extremely high chamber pressure.

This type of pressure relief is also useful as a mechanical method of determining the optimal cement properties for injecting into the patient line 19. In particular, as the cement cures, the pressure inside the chamber 24 increases significantly, and the force required to inject the cement increases concurrently. Thus, if the cement gets too hard, the high pressure sensed by the sensor 39 may actuate a visual indicator (not shown) to the operator that the cement has cured and can no longer be safely injected into the patient. Because the pressure is also a function of how fast the operator advances the ejection piston 25 if the operator depresses the piston 25 too quickly, the pressure will spike, and the valve 35 may be controlled to direct the cement into the shunt line 38 upon a maximum allowable pressure in the chamber 24 being sensed by sensor 39, in order to prevent the operator from injecting cement into the patient too quickly.

Because it is undesirable for the device 10 to burst or break into pieces while injecting cement, it may be desirable to incorporate a controlled failure mode. In particular, as the pressure increases in the delivery chamber, the torque on the piston 25/rod 27/handle 32 increases. A controlled failure mode can be designed in to these components so that they "fail" (i.e., stop driving the piston 25) at a known pressure inside the chamber 24 approaches a certain maximum pressure.

Another feature of the mixing/dispensing device 10 is that the components of the bone cement may be inserted by the user into, or come "pre-packaged" in, the chamber 24 of tubular body 21. For example, the components can be inserted into the mixing chamber 24 (with or without any pre-mixing) by the user through the proximal opening 40 by removal of the ejection piston assembly. Alternatively, some or all of the cement components may be pre-packaged in the chamber 24. For example, a solid component of the bone cement may be pre-packaged in the chamber 24 by the manufacturer, with a liquid component to be added by the user.

To operate the mixing/dispensing device 10, all ingredients of the cement must be present in the chamber 24. Thereafter, the opening 40 at the proximal end 22 is sealed by the ejection piston assembly (rod 27, piston 25, mixing disc 33 and/or impeller 34). The user mixes the ingredients together by moving the rod 27 back-and-forth relative to the tubular body 21, thereby employing one or both mixing implements 33 and 34. Notably, the ejection piston 25 is preferably left in a position about the proximal opening 40, with the stop ring 30 disengaged, during the mixing, so as to prevent premature expulsion of the cement contents from the chamber 24. By way of example, this may be accomplished by providing a latch (not shown) that holds the piston 25 in place at the opening 40 while the ingredients are being mixed.

In an alternate embodiment, the ejection piston assembly (rod 27, piston 25, mixing disc 33 and/or impeller 34) may be threaded into the interior wall of the tubular body 21, i.e., such that the piston assembly is moved distally through the chamber 24 by rotating the handle 32 to cause the mixing implement(s) 33 and/or 34 to move through the chamber 24 in a screw-like fashion. This embodiment may have the advantage of more precisely controlled ejection of the mixed cement from the chamber 24.

The user may additionally or alternatively employ manual shaking of the device 10 as part of the mixing process, if so desired. Notably, most known bone cements have a specific set up and cure time, so it is very important that the liquid component(s) of the cement are not mixed with the solid component(s) until just prior to use. Once the ingredients are thoroughly mixed, and the cement has cured to a desirable set point, the user fixes the stop ring 30 in a selected position along the rod 27, as shown in FIG. 1A, and depresses to allow the disc 25 to expel the product out of the opening 37 on the distal end 23 of the tubular body 21, as shown in FIG. 1B.

Figure 2:
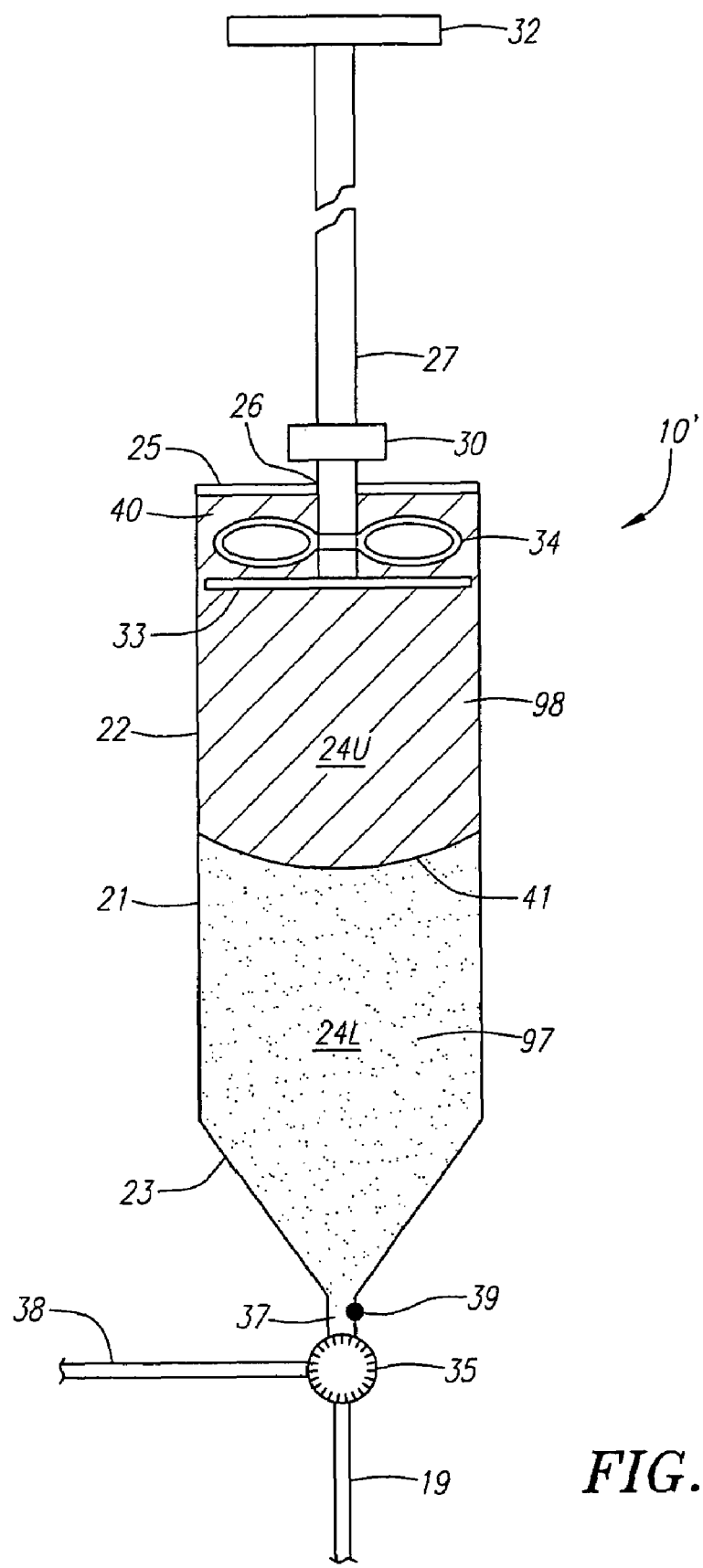
FIG. 2 is a cut-away, elevated side view of a second embodiment of a bone cement mixing/dispensing device, according to another aspect of the invention.

Alternatively, as shown in device 10' of FIG. 2, both a solid component and a liquid component of a bone cement may be pre-packaged by the manufacturer in the chamber 24. The pre-packed solid and liquid components must be separated from each other until mixing by a physical barrier 41, which divides the chamber 24 into two sub chambers, 24U the upper chamber and 24L the lower chamber. This barrier 41 may consist of plastic or another material that would rupture when moderate force is applied by the user. Preferably, the barrier 41 is made of a material that is easily breakable and non-reactive to the components—individually or the product of the mixture of the components. In addition, one of the components could be placed under a slight vacuum when sealed in order to aid in the mixing of the components. For example, the solid component could be placed under a vacuum so that, when the barrier 41 is ruptured, the liquid component is immediately drawn into the solid component.

Once the barrier is ruptured, the process of mixing and delivery in device 10' is substantially the same as described above for device 10 in FIGS. 1A and 1B.

It is important that a total and thorough mix of the cement ingredients takes place. Preferably, the tubular body 21 is made out of a transparent or a semi-transparent material, in order to allow the operator to visualize the mixing, transfer, and delivery of the cement in and from chamber 24, and also to allow the operator to identify the presence of any air bubbles in the cement mix.

Figure 3:
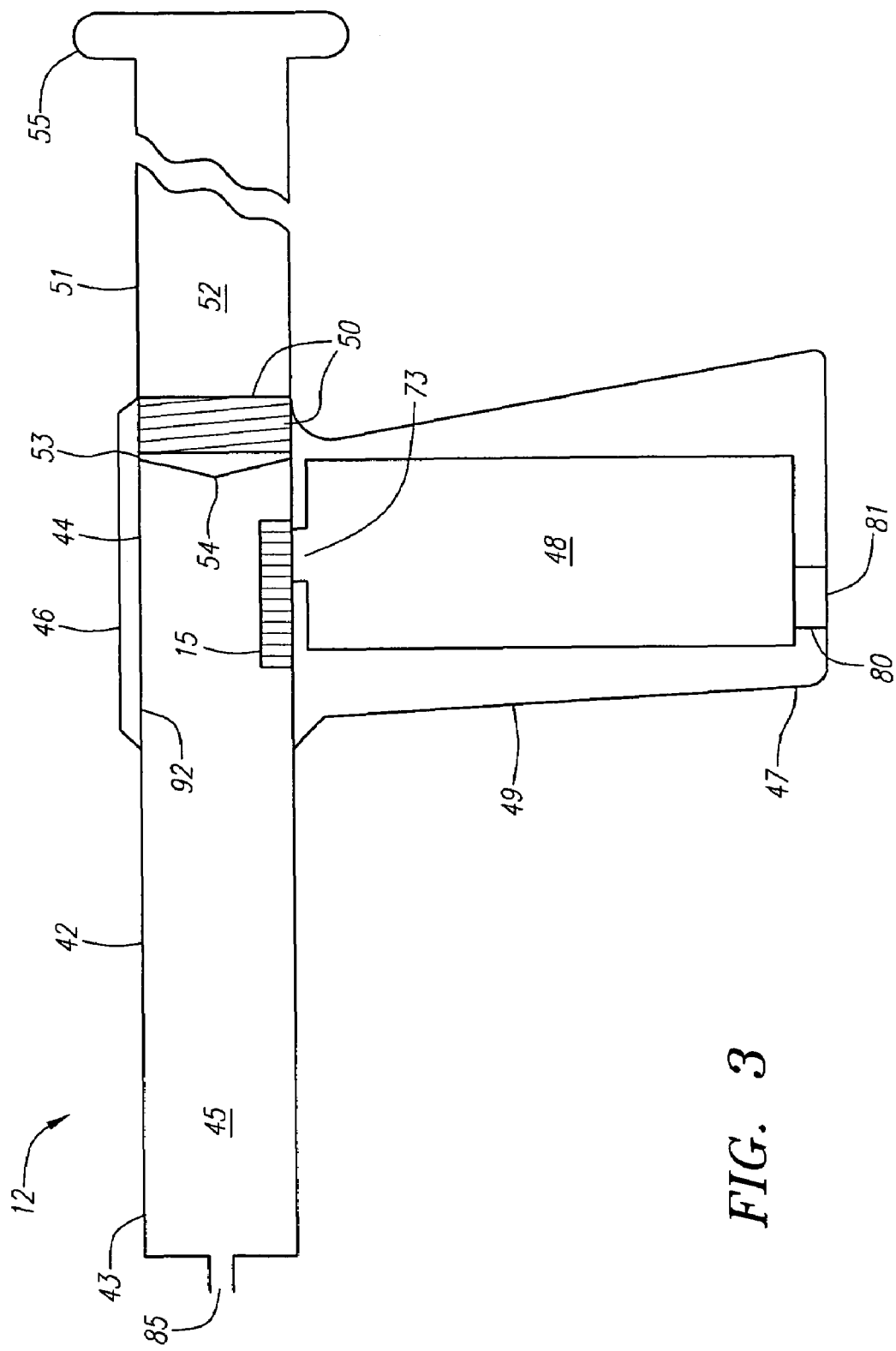
FIG. 3 is a cut-away, elevated side view of a further embodiment of a bone cement mixing/dispensing device, according to yet another aspect of the invention.

A further embodiment of a mixing and delivery device is shown in FIG. 3. The device 12 includes a first, tubular body 42 having a proximal end 43, a distal end 44, and forms a delivery chamber 45. The first body 42 is connected to a second body 49, the second body having a proximal end 46, a distal end 47, and forms a mixing chamber 48. Although any of a number of attachment mechanisms may be employed, in the illustrated device 12, the distal end 46 of the second body 49 forms a lumen 92, which is isolated from the mixing chamber 48 and sized for receiving the tubular first body 42 there through. The second body 49 may be connected to the first body 42 at any desired angle or in any mechanical relationship, so long as the delivery chamber 45 and mixing chamber 48 are in fluid communication with each other. In particular, an opening 73 in the mixing chamber 48 accesses the delivery chamber 45 through a valve 15, wherein the valve 15 may be switched between a first position which isolates the mixing chamber 48 from the delivery chamber 45, and a second position which places the respective chambers 45 and 48 in fluid communication.

In the illustrated device 12, the proximal end 46 of body 49 is connected to the distal end 44 of body 42 at an angle of slightly more than 90 degrees, i.e., resembling a pistol. This arrangement allows the second body 49 to be used as a "handle" to conveniently hold the device 12 during use. The proximal end 43 of the first body 42 has a cement extrusion opening 85 in communication with the delivery chamber 45. Connected to opening 85 (i.e., external to the device 12) may be the same valve and shunt tube assembly (35, 38, 19) shown in use with device 10 in FIG. 1. In addition, a sensor—such as sensor 39 of device 10—may also be used for controlling the output of device 12.

The distal 44 end of body 42 has an opening 50 sealed by a plunger 51. The plunger 51 consists of a rod 52 and a piston disc 53 connected to a distal end of the rod 52. The plunger 51 also has a handle 55 attached to the proximal end of the rod 52. The disc 53 preferably fits snuggly—but slidably—within the inside wall of the body 42, forming a movable seal to the delivery chamber 45. For example, a soft gasket (not shown) may be provided around the exterior circumference of the disc 53. The rod 52 has a sufficient length so that the disc 53 may be moved through the delivery chamber 45 and pressed against the (interior) distal end of the tubular body 42. The distal facing surface of the disc 53 is preferably slightly tapered, such that a raised portion 54 can extend into the opening 85.

In one embodiment, the plunger 51 is threaded into the interior wall of the tubular body 42, i.e., such that the plunger 51 is moved distally through the delivery chamber 45 by rotating the handle 55 to cause the plunger 51 to move along the threaded wall of the delivery chamber 45 in a screw-like fashion. This embodiment may have the advantage of more precisely controlled movement of the plunger 51 through the chamber 45.

An opening 80 is provided in the distal end 47 of the second body 49 for accessing the mixing chamber 48. A plug 81 seals the opening 80, the plug 81 being made of a material, e.g., silicon or rubber, that allows a needle to be inserted through the plug 81. In this manner, the chamber 48 can be pre-filled (e.g., by the manufacturer) with the solid component(s) of a cement to be mixed in the chamber 48. With the valve 15 in a "closed" (i.e., isolating) position, the user injects the liquid component into the chamber by piercing the plug 81 with a syringe containing the liquid cement component(s), and dispensing the liquid into the chamber 48. To mix the solid and liquid components together, the device 12 is shaken by the user.

After mixing the components together, the device 12 is inverted (with reference to FIG. 3), and—with the disc 53 moved proximal to opening 73, the valve 15 is switched to an open position. This allows the mixed cement product to flow from the mixing chamber 48 into the delivery chamber 45. Once the cement product is in the delivery chamber 45, the valve 15 is moved back to a closed position, and the device 12 is turned upright. The user can then dispense the mixed cement product through opening 85 by moving the plunger 51 distally through the delivery chamber 45. In alternate embodiments, the plunger 51 may be moved using a mechanical means such as a screw device (not shown). The movement may be controlled manually by the user, or could be controlled automatically.

Figure 4:
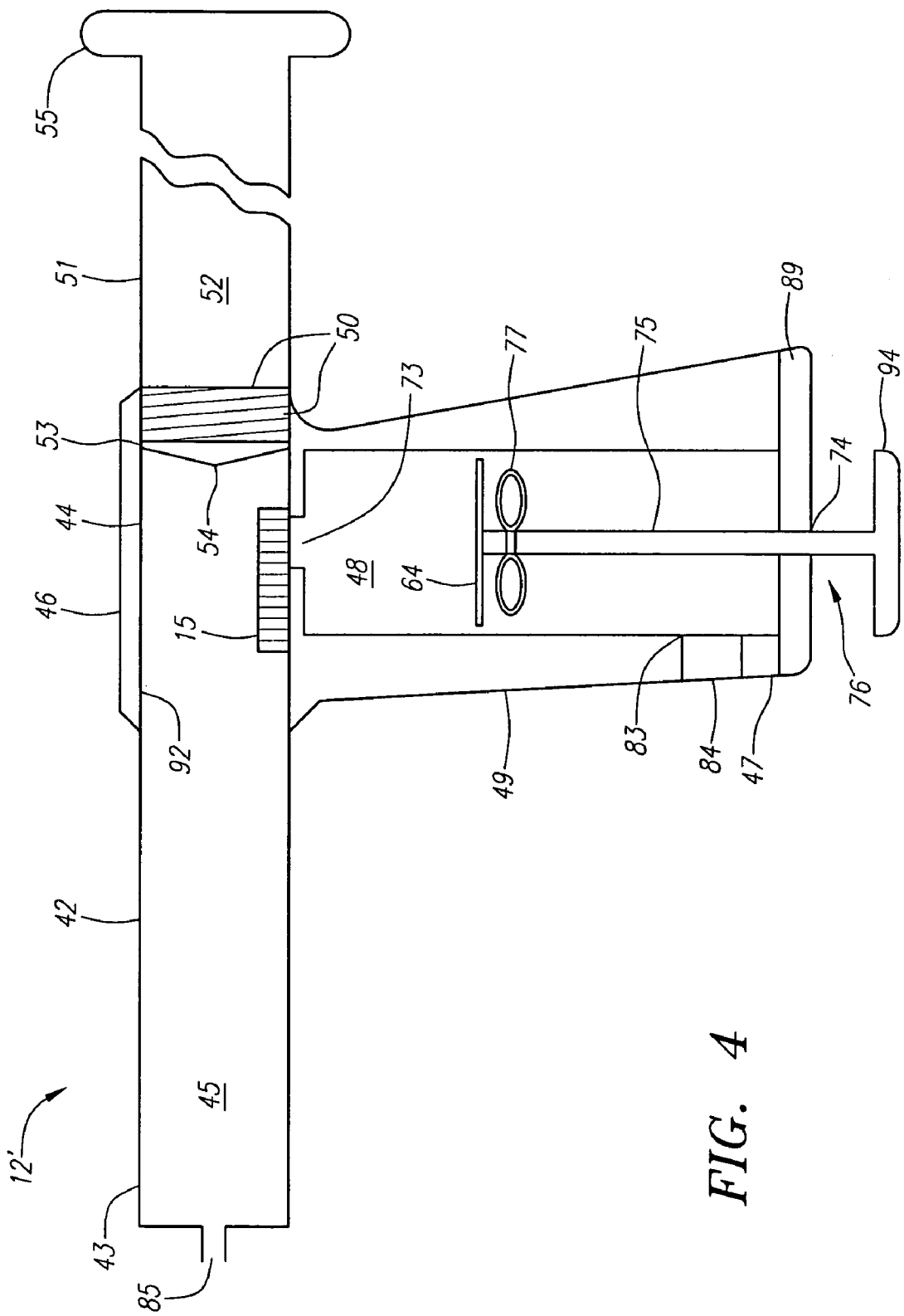
FIG. 4 is a cut-away, elevated side view of a further embodiment of a bone cement mixing/dispensing device, according to yet another aspect of the invention.

A variation of device 12 (referenced as 12') is shown in FIG. 4, which has the same features as device 12 of FIG. 3, with the addition of a mixing disc assembly 76 similar to the disc assembly (27/34/33) of FIG. 1A inserted through the distal end of the second body 49 and extendable through the mixing chamber 48. In particular, the device distal end 47 of the second body 49 in device 12' is provided with a gasket cap 89 with a central opening 74 through which a rod 75 extends into the mixing chamber 48. A handle 94 is attached to a proximal end of the rod 75. Again, a gasket or other sealing means (not shown) is preferably provided around the circumference of opening 74, such that the rod 75 moves slidably there through, in order to seal the chamber 48. Preferably, the rod 75 fits snuggly through the opening 74, but is movable relative to the body 49 without a user having to exert undue force.

A perforated mixing disc 64 is attached to the distal end of the rod 75. As the disc 64 is moved through the chamber 48, the contents in the chamber 48 are passed through the perforations (not shown) in the disc 64 and mixed. The size of the perforations in, and the outer circumference of, the mixing disc 33 may be varied, with these dimensions selected based on achieving the proper balance between adequately mixing the contents in the chamber 48, while allowing forward movement of the disc 64 without undue exertion on the part of the user. In the illustrated embodiment, a mixing impeller 77 is rotatably attached to the rod 75 just proximate (beneath) the mixing disc 64 to further facilitate mixing of the contents of the chamber 48. As with impeller 34 in the device 10 of FIG. 1A, the impeller 77 may comprise a plurality of angled mixing blades attached to a rotating collar on the rod 75, so that the blades are rotated around the rod 75 by force of the contents of the chamber 48 against the blades as the impeller 77 is moved through the chamber 48. It will be appreciated that alternate embodiments of the invention may be provided with only one of the perforated mixing disc 64 and impeller 77.

An opening 83 sealed with a plug 84 is provided in the side of the body 49, proximate distal end 47, for accessing the mixing chamber 48. The plug 84 is made of a material, e.g., silicon or rubber that allows a needle to be inserted through the plug 84. In this manner, the chamber 48 can be pre-filled (e.g., by the manufacturer) with the solid component(s) of a cement to be mixed in the chamber 48. With the valve 15 in a closed position, the user injects the liquid component into the chamber by piercing the plug 84 with a syringe containing the liquid cement component(s), and dispensing the liquid into the chamber 48. Alternately or additionally, the user may remove the cap 89 and mixing assembly 76 in order to place the components to be mixed into the chamber 48. Mixing is accomplished by moving the rod 75 with the mixing devices 64 and 77 through the chamber 48. To facilitate mixing the solid and liquid components together, the device 12' may be shaken by the user. Once the product is mixed, operation of the device 12' is substantially the same as for the device 12 shown in FIG. 3.

Again, it is preferable that the respective bodies 42 and 49 are made out of a transparent or a semi-transparent material, in order to allow the operator to visualize the mixing, transfer, and delivery of the cement in and from chambers 48 and 45, as well as to allow the operator to identify the presence of any air bubbles in the cement mix.

It is important that the inside of the mixing chamber is completely sealed and that the mixing chamber has no areas where unmixed cement polymer or monomer resides, as it is undesirable to have powder that does not mix with the monomer. Therefore the mixing disc and the proximal end of the mixing chamber should fit flush so that the disc comes into contact with all of cement. To ensure complete mixing, it is desirable that the inside surface of the proximal end of the mixing chamber be flat when the surface of the mixing disc that contacts the bottom of the chamber is flat. Similarly, it is possible for both surfaces to be convex or concave, or any other shape, as long as the mating surfaces fit flush with each other when the disc contacts the end of the mixing chamber that is adjacent the delivery chamber.

Figure 5A:
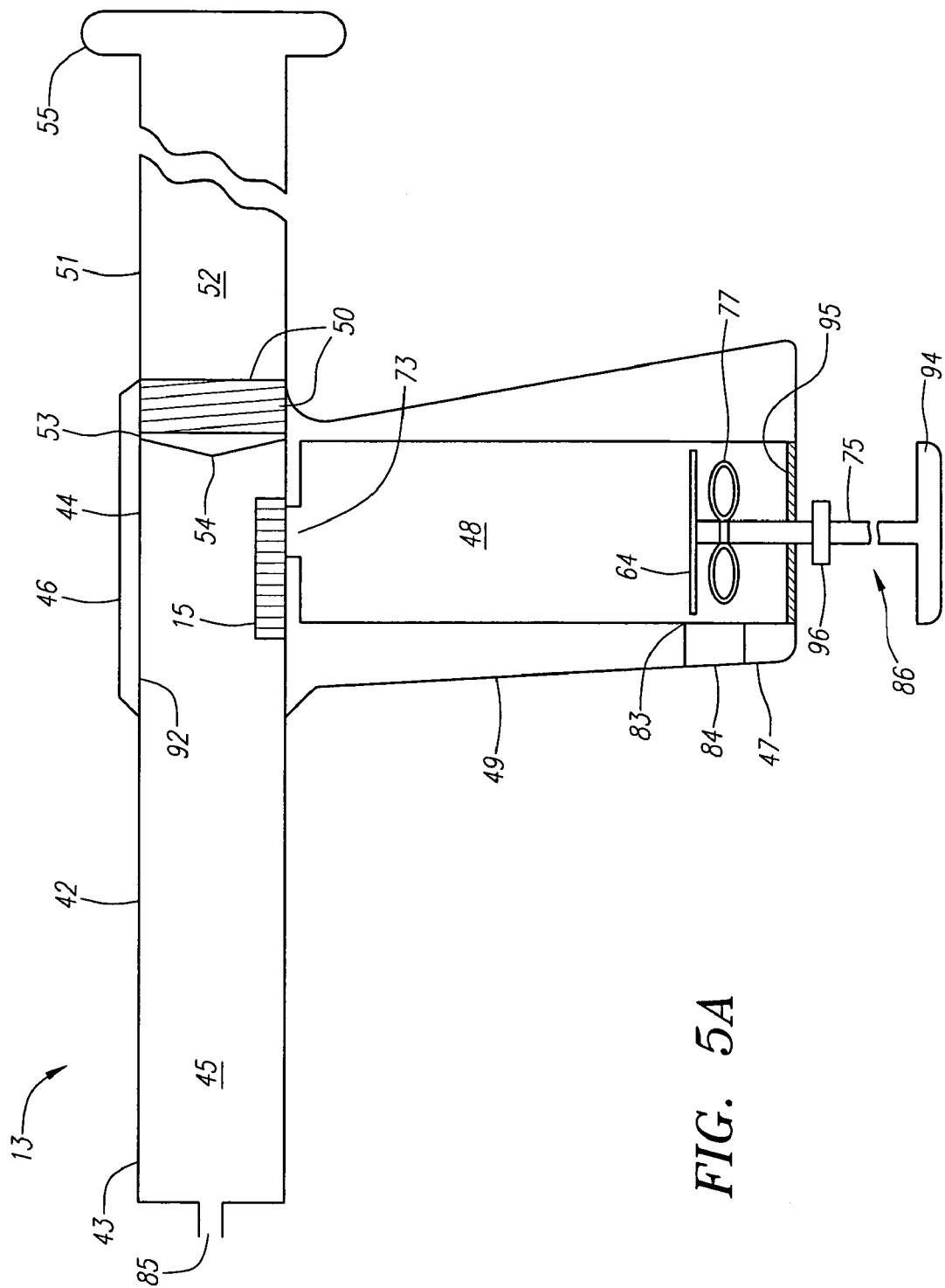
FIGS. 5A and 5B are cut-away, elevated side views of a still further embodiment of a bone cement mixing/dispensing device, according to yet another aspect of the invention.
Figure 5B:
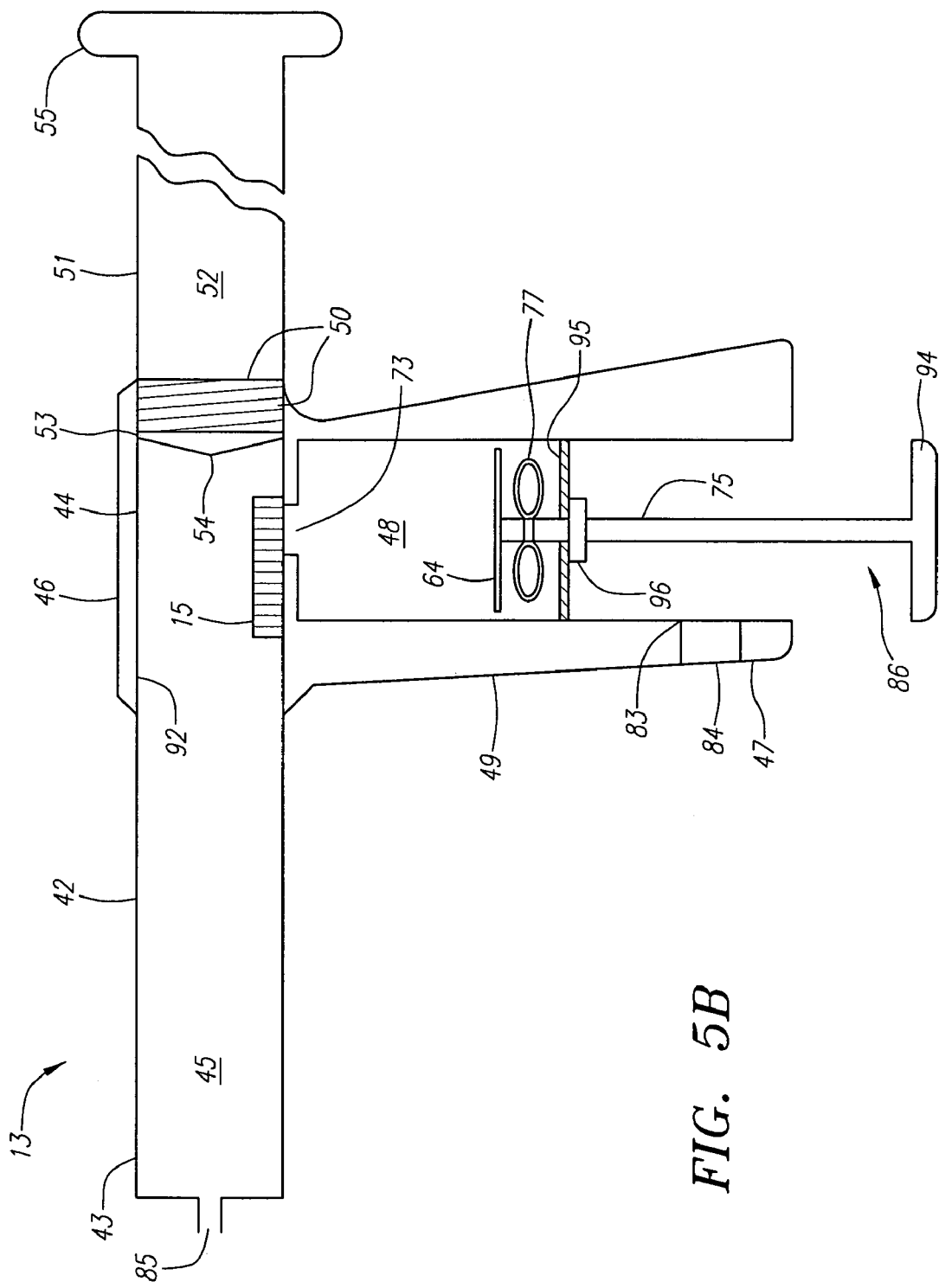

FIGS. 5A and 5B illustrate yet another mixing and delivery device 13 constructed in accordance with yet another aspect of the invention, which combines the features of device 12' of FIG. 4, with the movable dispensing piston/disc of device 10 of FIGS. 1A and 1B. In particular, the distal end cap 89 of device 12' is removed, and the mixing assembly 76 is replaced with a combined mixing and dispensing assembly 86 in device 13, in which the distal opening of body 49 is sealed by a movable ejection piston 95. The ejection piston 95 has an outer circumference sized to snuggly fit in the inner circumference of the chamber 48. A gasket, or other type of sealing means (not shown) may be disposed about the periphery of the piston 95 to prevent the cement contents in the chamber 48 from passing between the piston 95 and chamber wall. In an alternate embodiment, a separate (preferably removable) cover may be provided to seal the chamber 48 separate from the ejection piston 95.

The piston 95 has a central opening through which rod 75 extends into the chamber 48. Again, a gasket or other sealing means (not shown) is preferably provided around the circumference of opening in piston 95, such that the rod 75 moves slidably there through, in order to maintain the sealing of chamber 48. Preferably, the rod 75 fits snuggly through the opening in piston 95, but is movable relative to body 49 without a user having to exert undue force. In alternate embodiments, the rod 75 may be fixed to the piston 95, or a latch mechanism (not shown) may be employed to allow the user to selectively fix the rod 75 to the piston 95.

In device 13, a stop ring 96 is selectively placed around the rod 75 to limit the distance that the rod 75 may be extended into the chamber 48. Preferably, a user of the device 13 may fix the stop ring 96 at a desired position along the length of the rod 75, although it may also be fixed to begin with. By way of non-limiting example, the stop ring 96 may be compliant and create a snug fit that remains movably, stretched around about the rod 75. Alternately, the stop ring 96 may be fixed to the rod 75 using a locking screw. As is illustrated in FIG. 1B, as the rod 75 is moved relative to body 49 and into chamber 48, the stop ring 96 engages piston 95, causing piston 95 to be moved through chamber 48 along with the rod 75. The valve 15 must be opened prior to movement of the piston 95, or compression of the contents in chamber 48 would impede movement, or encourage leakage past the seal between the piston 95 and the body 49.

Figure 6A:
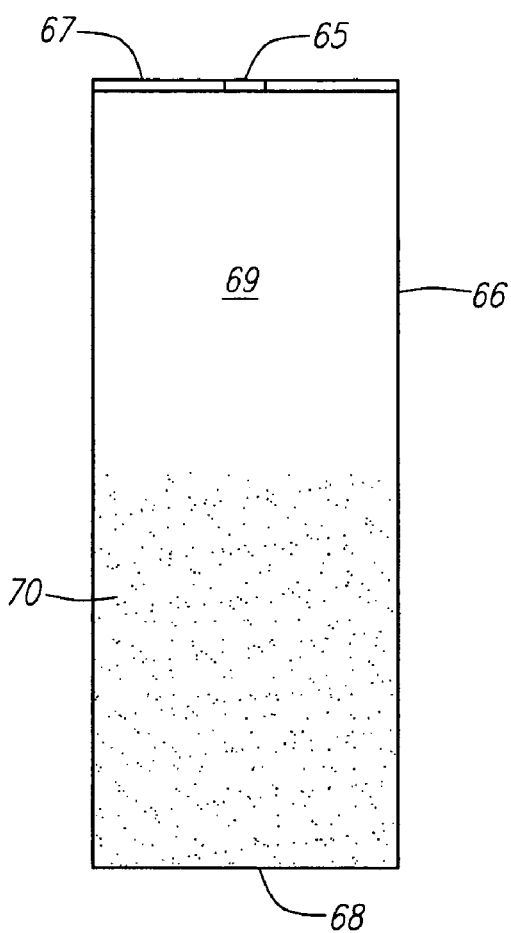
FIGS. 6A and 6B are cut-away, elevated side views of a separate mixing cartridge that may be optionally used with a bone cement mixing/dispensing device, according to still another aspect of the invention.
Figure 6B:
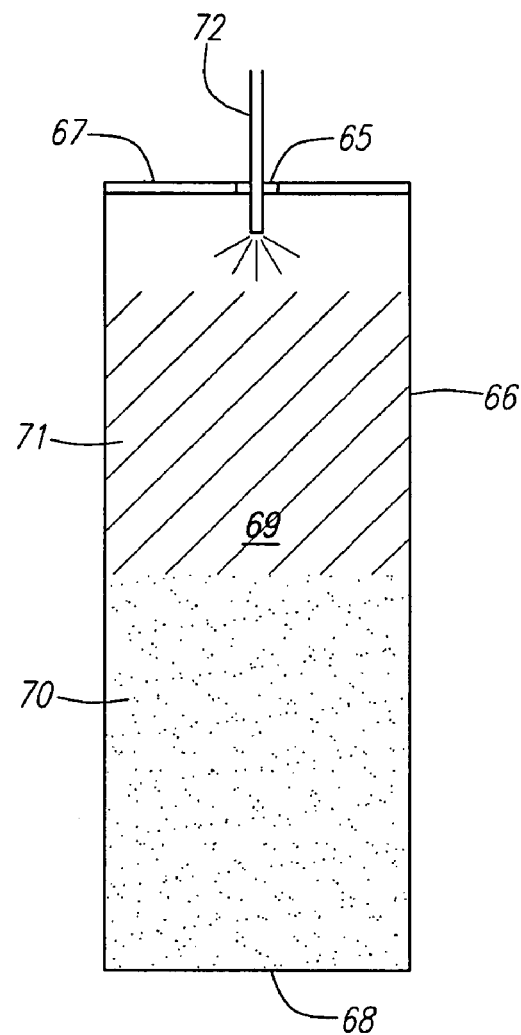

Referring now to FIGS. 6A and 6B, in accordance with yet another aspect of the invention, a removable mixing cartridge 66 may be optionally used in conjunction with a delivery device, such as devices 12, 12' or 13 shown in FIGS. 3, 4 and 5A-B. It will be apparent the minor modifications to the mixing body 49 may be made in order to accommodate the cartridge 66, which is sized to fit in chamber 48, e.g., in a snap-in locking arrangement. The cartridge forms a sealed chamber 69, which is pre-filled with the solid component(s) .70 of a bone cement. A first end 67 of the cartridge 66 is provided with a sealed opening 65, through which a needle 72 can be inserted to inject the liquid bone cement component(s) 71. After the liquid components(s) 71 are added, the cartridge 66 is shaken (not stirred), to mix the cement ingredients. The cartridge 66 may be designed with an integral mixing paddle (not shown) sealed within the cartridge 66 to facilitate the mixing that is performed by shaking the cartridge. The cartridge 66 is then inserted into the second body 49 (i.e., through the distal opening in place of the mixing assembly 76 or 86). The same opening 65 used to insert the liquid cement components 71 into chamber 69 may be aligned with the opening of the valve 15 for communication of the cement contents into the delivery chamber 45. Alternatively, access may be had through an opposite end 68 of the cartridge 66.

As will be apparent, in alternate embodiments, both of the solid and liquid cement components 70 and 71 may be pre-placed in the cartridge 66, e.g., with a barrier isolating the ingredients until the cartridge is sufficiently shaken to break the barrier. As will also be apparent, the mixing assembly 76 or the mixing and dispensing assembly 86, or some variation thereof, be employed after the cartridge 66 is placed in the body 49, as described above.

Figures 7A, 7B, 7C:
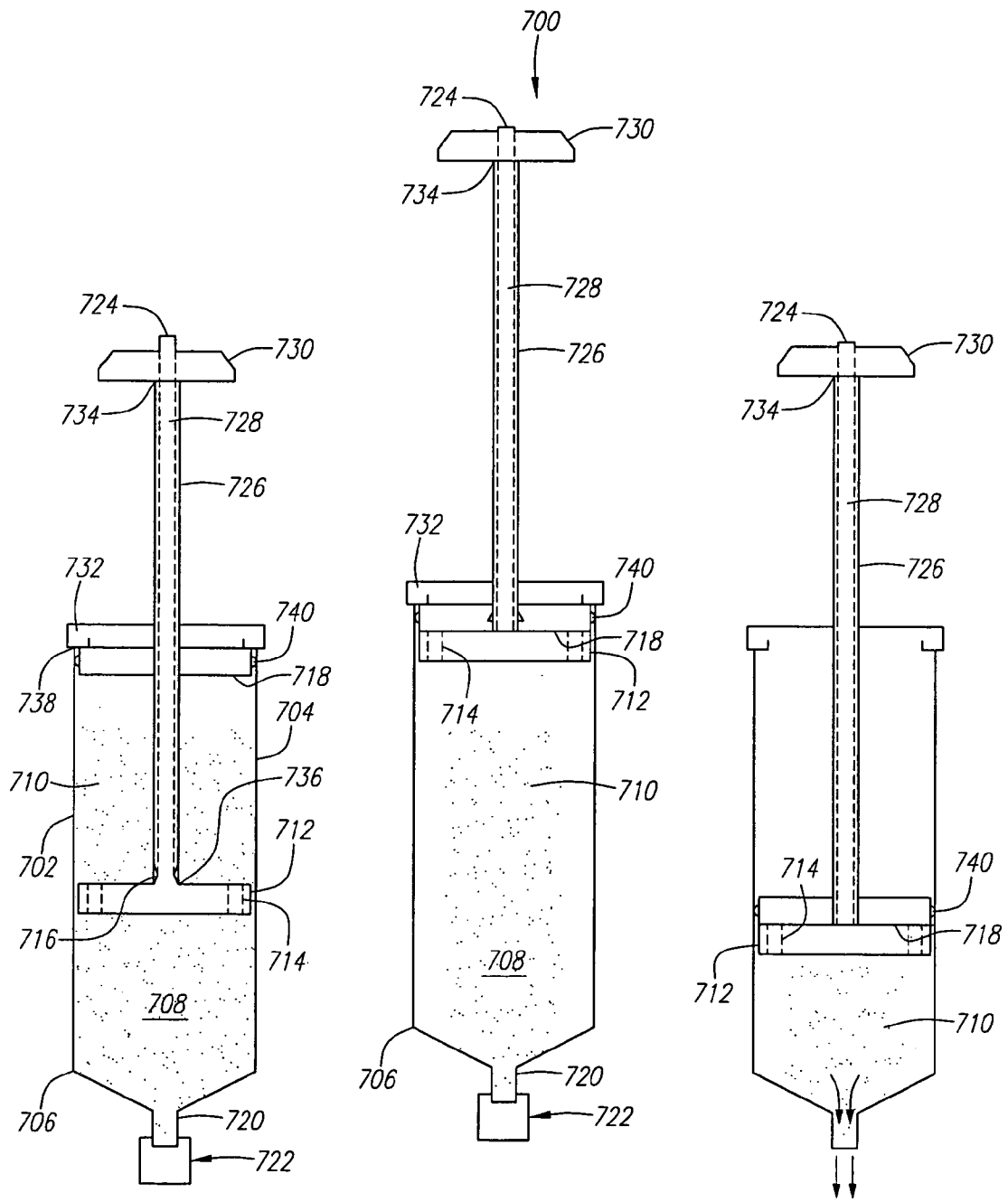
FIGS. 7A-7C are cut-away, elevated side views of an embodiment of a bone cement mixing/dispensing device according to another aspect of the invention.

Turning next to FIGS. 7A through 7C, in accordance with another aspect of the invention, a device 700 for mixing and dispensing a bone cement, to a cannula (not shown) inserted into a selected body cavity (also not shown) is illustrated. Generally, the device 700 includes a tubular body 702, such as a syringe, a rod 726, a mixing disc 712, and a moveable ejection piston 718.

The tubular body 702 has a proximal portion 704 and a tapered distal portion 706, defining an internal mixing chamber 708, within which a bone cement 710 and/or biomaterials may be mixed and stored. The tapered distal portion 706 has a narrow opening 720 in communication with the internal chamber 708. A luer lock or other connector 722, may be provided on the opening 720 for cooperating with a complementary connector on a cannula (not shown) to facilitate delivery of the bone cement 710 to a treatment site. The connector 722 may also have a cap (not shown) or other means for preventing the bone cement 710 from leaking out through the opening 720 during the mixing process.

The moveable ejection piston 718 is separate from the tubular body 702 and the rod 726 and is contained within the proximal portion 704 of the internal chamber 708. The ejection piston 718 has an outer circumference sized to snuggly fit in the inner circumference of the tubular body 702. A gasket, o-ring 740 or other type of sealing means may be disposed about the periphery of the ejection piston 718 to prevent the bone cement 710 in the internal chamber 708 from passing between the ejection piston 718 and internal wall of the tubular body 702. The ejection piston 718 has a central opening (not shown) through which the rod 726 extends into the internal chamber 708. A gasket or other sealing means (not shown) may be provided around the circumference of the opening such that the mixing rod 728 moves slidably therethrough. During the mixing process, the ejection piston 718 is stationary and preferably attached to a removable cover 732 located at the proximal end 738 of the tubular body 702. The ejection piston 718 may be mechanically attached to the removable cover 732 by any means known to those of skill in the art.

The mixing disc 712 is attached at a distal end of the rod 726. The mixing disc 712 has multiple perforations 714 designed to facilitate the mixing of the bone cement as described previously. At the proximal end 734 of the rod 726 there is a handle 730. The rod 726 has an axial lumen 728 that extends from a button 724 located on the handle 730 to the distal end 736. The rod 726 is configured such that the button 724 controls a locking mechanism 716. The locking mechanism 716 is designed to engage the ejection piston 718.

To operate the mixing/dispensing device 700, all ingredients of the bone cement must be in the internal mixing chamber 708. Thereafter, the user mixes the ingredients together by moving the rod 726 back and forth relative to the tubular body 702, as well as possibly rotating the rod 726 about its central axis, this action causes the mixing disc 712 to pass through the multi-component cement and blend the components together. The ejection piston 718 remains in place at the proximal end 738 of the tubular body 702 during the mixing process.

Once the mixing process is complete, the user may selectively engage the ejection piston 718 when it is desirable to dispense the bone cement 710. To engage the ejection piston 718, the rod 726 is pulled axially to move the mixing disc 712 toward the proximal end 738 of the tubular body 702 adjacent to the ejection piston 718. The button 724 is depressed, activating the locking mechanism 716 to engage the ejection piston 718 with the rod 726 as illustrated in FIG. 7B. As depicted, the locking mechanism 716 comprises tabs, which extend out from the rod 726 to lock onto the ejection piston 718. This mechanism is illustrative and not intended to be a limitation on the type of mechanism suitable in this application. The locking mechanism 716 operates to allow the mixing disc 714 and the ejection piston 718 to adjoin. Once the ejection piston 718 is locked in place, the mixing disc 712 and the ejection piston 718 move distally together to dispense cement as shown in FIG. 7C.

In an alternative embodiment, the rod 726 may be threaded and designed to mate with a threaded bracket (not shown) attached above the cover. In this alternative, the bracket has a quick release mechanism. After the mixing, as described above, is completed, the threaded bracket is engaged such that the rod is moved distally through the tubular body by rotating the handle to cause the rod with the ejection piston and mixing disc to move through the tubular body in a screw like fashion to dispense the bone cement.

FIG. 8A illustrates a combination mixing/dispensing rod 800 in accordance with an embodiment of the invention. The mixing/dispensing rod 800 generally comprises a rod 802 having a distal end 804, and a proximal end 806. Located at the proximal end 806 of the rod 802 is a handle 810. At the distal end 804 of the rod 802 are two mixing discs, a first mixing disc 820 and a second mixing disc 830. The first and the second mixing discs 820, 830 have outer circumferences sized to snuggly fit in the inner circumference of a tubular body, such as that shown in FIGS. 7A-7C.

FIG. 8B illustrates an embodiment of the first mixing disc 820. The first mixing disc 820 has multiple perforations 822 (*a-d*) sized such that a bone cement may pass through the perforations 822(*a-d*) and be adequately mixed while allowing movement of the mixing/dispensing rod 800 without undue exertion. While illustrated as having four perforations 822(*a-d*), this is not intended to be a limitation on the number of perforations that the first mixing disc 820 may have. A gasket, o-ring 814 or other type of sealing means may be disposed about the periphery of the first mixing disc 820 to minimize the bone cement which remains in the tubular body (not shown) after dispensing the bone cement. The first mixing disc 820 further includes clips 824(*a-h*) to aid in locking the first mixing disc 820 to the second mixing disc 830 when the perforation are aligned as described below.

FIG. 8C illustrates an embodiment of the second mixing disc 830, also having multiple perforations 832(*a-d*). Similar to the first mixing disc 820, the perforations 832(*a-d*) in the second mixing disc 830 are designed to allow a bone cement to pass through the perforations, while still allowing movement of the mixing/dispensing rod without undue exertion. As with the first mixing disc, the number of perforations shown is not intended to be a limitation on the number of perforations that the second mixing disc 830 may have.

The perforations 822(*a-d*) on the first mixing disc 820 and the perforations 832(*a-d*) on the second mixing disc 830 are in a pattern such that the perforations may be aligned as shown in FIG. 8D. When aligned, the bone cement may pass through the perforations on both the first and the second mixing discs 820, 830 allowing the mixing/dispensing rod 800 to be used for mixing the bone cement. The clips 824(*a-h*) act to hold the perforations 822(*a-d*) in line with the perforations 832(*a-d*). The clips 824(*a-h*) maybe tension clips that can be released with minimal pressure. Alternate means, such as a locking mechanism on the rod, of assuring the perforations on the first and the second mixing discs 820, 830 remain aligned are equally applicable for use in this embodiment.

In addition, the perforations 822(*a-d*) on the first mixing disc 820 and the perforations 832(*a-d*) on the second mixing disc may be offset as depicted in FIG. 8E. When offset, the perforations 822(*a-d*) of the first mixing disc 820 are sealed by the non-perforated area on the second mixing disc 830 and visa versa. This arrangement permits the mixing/dispensing rod 800 to be used to dispense the bone cement.

Preferably the number, shape and size of the perforations in the first mixing disc 820 and the second mixing disc 830 are the same so that the perforations may easily be aligned or offset.

When the mixing/dispensing rod 800 is implemented in mixing the bone cement, the perforations 822(*a-d*), 832(*a-d*) are aligned and the clips 824(*a-h*) are engaged. The mixing of the bone cement is done in a conventional manner as described previously. After the bone cement is thoroughly mixed and prepared to be dispensed, the mixing/dispensing rod 800 is pulled to a far proximal end of a mixing chamber. The mixing rod handle 810 is then rotated releasing the clips 824(*a-h*) so that the perforations 822(*a-d*), 832(*a-d*) are offset, e.g., in the embodiment, the first mixing disc 820 is rotated approximately 45 degrees relative to the second mixing disc 830. Offsetting the perforations results in the blocking of the perforations on both the first mixing disc 820 and the second mixing disc 830. The first and the second mixing disc 820, 830 together then form an ejection piston, and the bone cement is dispensed by pushing the rod 802, and the first and the second mixing discs 820, 830, distally.

FIG. 9 illustrates another combination mixing/dispensing rod 900 having a locking mechanism to engage an ejection piston 910 to a mixing disc 930. The mixing/dispensing rod 900 generally comprises a rod 902 having a proximal end 904 and a distal end 906. Located at the proximal end 904 of the rod 902 is a handle 908. Located at the distal end 906 of the rod 902 is a mixing disc 930. The mixing disc 930 has a multiple perforations 932 to facilitate the mixing of a bone cement. Also located near the distal end 906 of the rod 902 is a lock rod mechanism 912. The lock rod mechanism 912 may engage the ejection piston 910 and lock the ejection piston 910 in place adjoining the mixing disc 930.

FIG. 9A illustrates the mixing/dispensing rod 900 configured to mix the bone cement. In this configuration, the ejection piston 910 is secured the handle 908. When the mixing/dispensing rod 900 is assembled to mix, the perforations 932 in the mixing disc 930 are unobstructed and the bone cement is free to pass through the perforations as the mixing disc 930 is moved axially through the bone cement. The ejection piston 910 may be secured to the handle 908 by any means known in the art, for example, it may be secured in a mechanical means by locking extensions 916 as illustrated and as described below.

FIG. 9B illustrates the mixing/dispensing rod 900 configured to dispense the bone cement. In this configuration, the ejection piston 910 is secured to the mixing disc 930 at the distal end of the rod 902. When the mixing/dispensing rod 900 is arranged to dispense the bone cement, the ejection piston 910 abuts the mixing disc 930 and blocks the perforations 932 thereby preventing the flow of bone cement through the mixing disc 930. The ejection piston 910 may be secured to the mixing disc 930 by any means known in the art, for example, it may be secured in by mechanical means such as a lock pin 912 as illustrated and described below.

FIG. 9C is a plan view of the exemplary ejection piston 910. The ejection piston 910 is a solid disc designed to force a bone cement through a mixing chamber (not shown) such as the chamber 48 of FIG. 4A or the chamber 708 of FIG. 7. A gasket, o-ring 914 or other type of sealing means may be disposed about the periphery of the ejection piston 910 to prevent the bone cement in the mixing chamber from passing between the ejection piston 910 and an internal wall of the mixing chamber. The ejection piston 910 is configured to mate with the interior surface of the handle 908 such that the ejection piston 910 can be held in place abutting the handle 908. In order to accomplish the mating, the ejection piston 910 may have locking extensions 916 that are designed to extend into the handle 908. The locking extensions 916 prevent the piston 910 from accidentally disengaging from the handle 908. The locking extensions may be controlled via a push button 934 located on the handle 908. While the locking extensions 916 are shown to extend vertically from the ejection piston 910 into the handle 908, this is not intended to be a limitation on the mechanism for attaching the ejection piston 910 to the handle 908. Any mechanism capable of holding the ejection piston 910 in place, that is readily releasable, is suitable for use in the invention, e.g. a lock rod mechanism such as the one described below that adjoins the ejection piston 910 to the mixing disc 930. The ejection piston 910 is further configured with grooves 920 for engaging the lock rod mechanism 912 as described below.

After the bone cement is mixed in the manner described in conjunction with previous figures, the ejection piston 910 is released from the handle 908 by depressing the push button 934. The ejection piston 910 is then secured at the distal end 906 of the rod 902 as illustrated in FIG. 9B. The ejection piston 910 abuts the mixing disc 930 and is held in place by the lock rod mechanism 912. The lock rod mechanism 912 engages the ejection piston 910 and prevents the ejection piston 910 from moving independent of the rod 902 while at the same time holding the ejection piston 910 adjacent to the mixing disc 930. The lock rod mechanism is engaged by axially pulling the rod 902 to a proximal end of a mixing chamber. Once the rod 902 has been pulled to the proximal end, the lock rod mechanism 912 is aligned with the grooves 920 on a distal surface 918 of the ejection piston 910. The handle 908 is then rotated to engage the lock rod mechanism 912 with the grooves 920 on the distal surface 918 of the ejection piston 910. This rotation fastens the ejection piston 910 to the rod 902. After the ejection piston 910 is locked in place, the rod 902 is pushed distally inside a chamber causing the mixing disc 930 and the ejection piston 910 to dispense the mixed bone cement. The ejection piston 910 covers the perforations in the mixing disc 930 preventing the bone cement from passing through the perforations and forcing the bone cement toward a distal end of the chamber.

Figure 10:
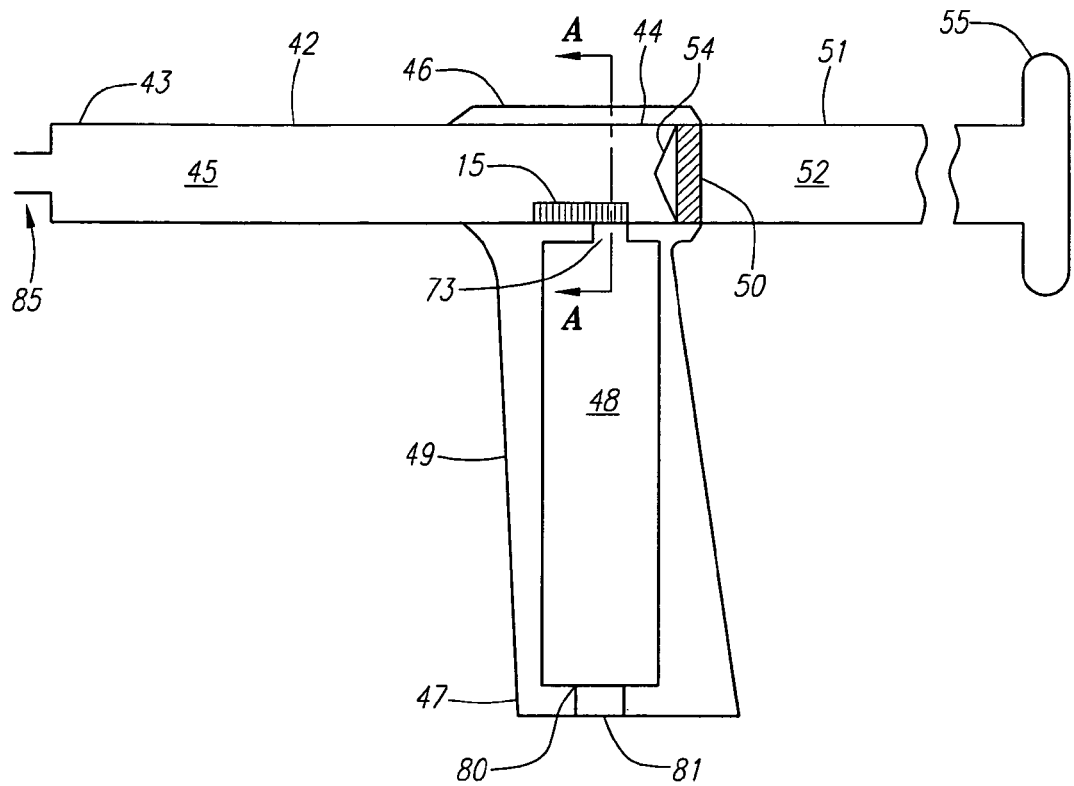
FIG. 10 is a reproduction of the embodiment of FIG. 3.
Figure 10A:
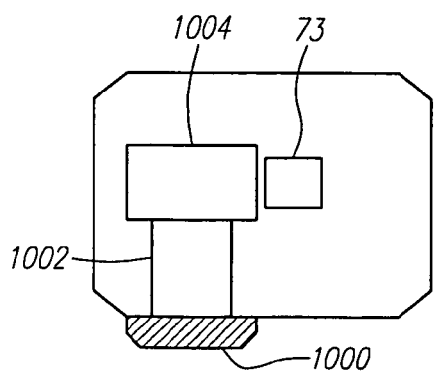
FIGS. 10A and 10B are plan views of an embodiment of a valve for use in the bone cement mixing/dispensing device of FIG. 4.
Figure 10B:
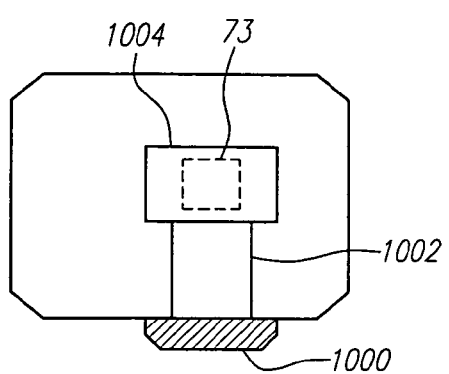

FIGS. 10A and 10B depict a valve 1000 configured for use as the valve 15 in a bone cement delivery device such as the devices depicted in FIG. 3, FIG. 4 or FIGS. 5A and 5B. For the reader's ease, the embodiment of FIG. 3 is reproduced in FIG. 10. It is undesirable to have any portion of the powder component unmixed with the liquid component. Optimally, the inside surface of the proximal end of the mixing chamber should have the same profile as the mixing disc. For example, if the mixing disc has a flat profile, the inside surface of the end of the mixing chamber 48 should also be flat. However, this creates other challenges, as the mixing chamber 48 must be in fluid communication with the delivery chamber 45. Therefore, if the mixing chamber 48 and delivery chamber 45 are coupled via a valve, then the valve must also have the same geometry as the mixing disc so that the valve sits flush with the inside surface of the end of the mixing chamber 48.

FIGS. 10A and 10B are plan views of the valve 1000 at the section A-A in FIG. 10. The valve 1000, is a sliding apparatus that provides for fluid communication between the mixing chamber 48 and the delivery chamber 45. The valve 1000 comprises a moveable part 1004 that opens, shuts, or partially obstructs the opening 73, thereby controlling the flow of the bone cement. The moveable part 1004 is controlled by an arm 1002, which extends from the valve 1000. The moveable part 1004 is a slide, which moves along the axial length of the delivery chamber 45. The geometry of the moveable part 1004 is such that is has the same profile as the inside end surface of the chamber, e.g., is a flat member. FIG. 10A depicts the valve 1000 in an open position, with the moveable part 1004 not obstructing the opening 73. FIG. 10B depicts the valve 1000 in a closed position with the moveable part 1004, covering the opening 73 thereby preventing the bone cement from passing from the mixing chamber 48 to the delivery chamber 45. In the closed position, the valve 1000 also prevents the flow of the material back into the mixing chamber 48 after it has been moved to the delivery chamber 45.

Figure 11A:
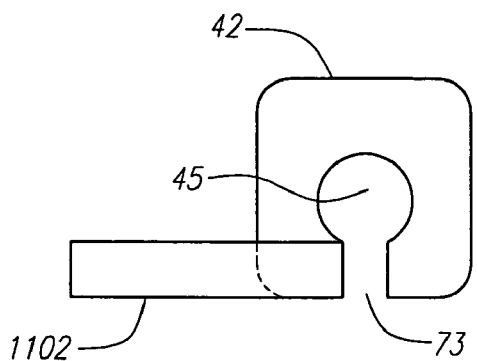
FIGS. 11A and 11B are cross-section views of another embodiment of a valve for use with the bone cement mixing/dispensing device of FIG. 4.
Figure 11B:
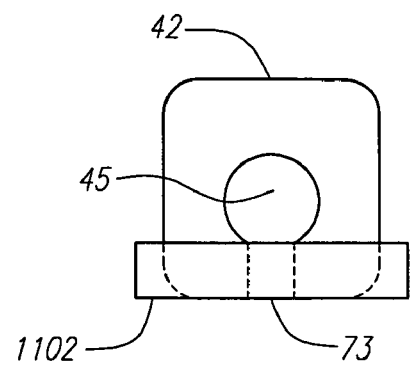

FIGS. 11A and 11B depict another embodiment of a valve configured for use as the valve 15 in a bone cement delivery device such as the devices depicted in FIG. 3, FIG. 4 or FIGS. 5A and 5B. FIGS. 11A and 11B are cross sections of the valve taken along the line A-A on reproduced FIG. 3. The valve generally operates in the same manner as the valve 1000 and comprises a moveable part 1102. The moveable part 1102 is a slide, which moves across the axial length of the delivery chamber 45. FIG. 11A depicts the valve 1100 in an open position, with the moveable part 1102 not obstructing the opening 73. FIG. 11B depicts the valve 1100 in a closed position with the moveable part 1102, covering the opening 73 thereby preventing the bone cement from passing from the mixing chamber 48 to the delivery chamber 45. The moveable part 1102 is pushed through the cross-section of the delivery chamber 45. While illustrated as moving across the axial length, one skilled in the art will appreciate that the moveable part may be designed to cross the delivery chamber 45 in any direction other than axially aligned with the delivery chamber 45

In alternative embodiments of the valves depicted in FIGS. 10A, 10B, 11A, and 11B, the moveable parts 1004, 1102 are constructed such that each has a passage through it that that allows for fluid communication. When the moveable part 1004, 1102 is slid engaging the valve, as described in conjunction with FIGS. 10A, 10B, 11A, and 11B, the passage in the moveable part 1004, 1102 may be aligned with the opening 73 in the delivery chamber 45 and the bone cement is allowed to flow from the mixing chamber 48 to the delivery chamber 45. When the passage is not aligned with the opening, the bone cement is prevented from flowing between the mixing chamber and the delivery chamber.

In operation, the bottom of the mixing chamber must be able to communicate via the valve with the delivery chamber. Therefore, moveable part of the valve is designed to seal flat or flush with the mixing disc. Although depicted as flat in the illustrated embodiments the shape of the moveable part may vary to complement the profile of the mixing disc and of the mixing chamber.

Figure 12A:
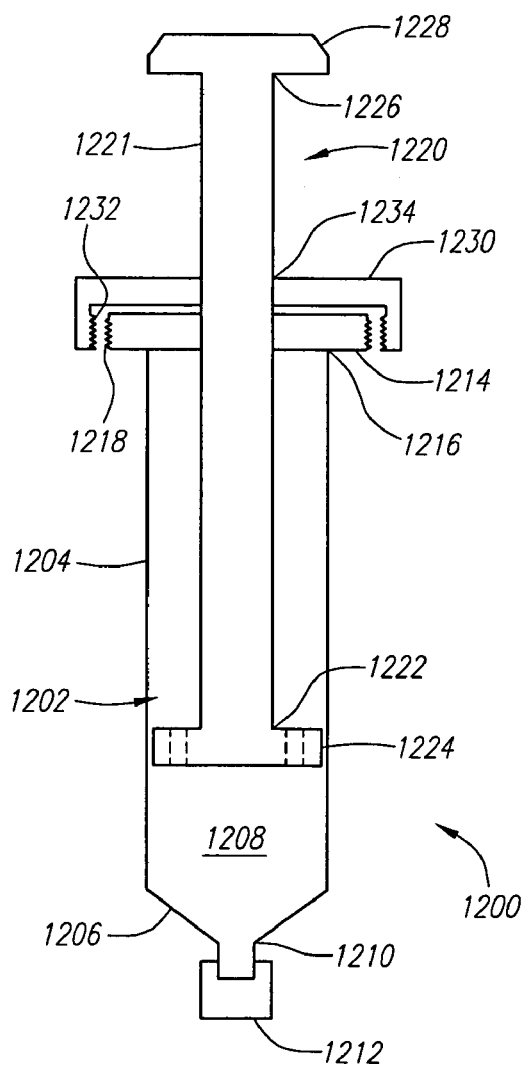
FIGS. 12A and 12B are cut-away elevated side views of still another embodiment of a bone cement mixing/dispensing device according to another aspect of the invention.
Figure 12B:
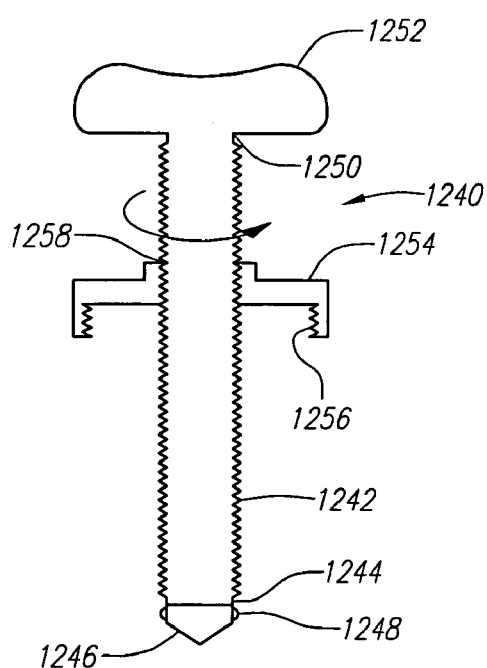

FIG. 12 is yet another device for mixing and dispensing a bone cement to a cannula (not shown) inserted into a selected body cavity (also not shown). Generally, the device 1200 includes a mixing/dispensing chamber 1202 (FIG. 12A), a mixing rod 1220 (FIG. 12A) and a piston rod 1240 (FIG. 12B).

The mixing/dispensing chamber 1202 has a proximal portion 1204 and a tapered distal portion 1206, defining an internal chamber 1208, within which a bone cement and/or biomaterials (not shown) may be mixed and then dispensed. The tapered distal portion 1206 has a narrow opening 1210 in communication with the internal chamber 1208. A luer lock 1212 or other connector may be provided on the opening for cooperating with a complementary connector on the cannula to facilitate delivery of the bone cement to a treatment site. The connector may also have a cap (not shown) or other means for preventing the bone cement from leaking out through the opening 1210 during the mixing process. The proximal portion 1204 has a brim 1214 located at a far proximal end 1216. The brim 1214 has a threaded edge 1218 for mating with a removable cover that may be placed on the mixing/dispensing chamber 1202 as described below.

The mixing rod assembly 1220 generally comprises a rod 1221 having a distal end 1222 and a proximal end 1226. Located at the distal end 1222 of the rod 1221 is a perforated mixing disc 1224. At the proximal end 1226 of the rod 1221 is a handle 1228. Also located along the axial length is a cover 1230 sized to enclose the proximal end 1216 of the mixing/dispensing chamber 1202. The inner circumference 1232 of the cover 1230 has complementary threads for mating with the threads 1218 on the brim 1214. The cover has an opening 1234 through which the rod 1221 may pass. Preferably the rod 1221 fits snuggly through the opening 1234 but is moveable relative to the cover 1230 without a user having to exert undue force. A gasket or other sealing means (not shown) may be provided around the circumference of the opening 1234 to provide a seal while still allowing the rod 1221 to move slidably there through.

The dispensing rod assembly 1240 generally comprises a threaded rod 1242 having a distal end 1244 and a proximal end 1250. Located at the distal end 1244 of the threaded rod 1242 is a piston 1246. A gasket, o-ring 1248 or other type of sealing means may be disposed about the periphery of the piston 1246 to prevent the bone cement in the internal chamber 1208 from passing between the piston 1246 and internal wall of the mixing/dispensing chamber 1202. At the proximal end 1250 of the threaded rod 1242 is a handle 1252. Also located along the axial length is a cover 1254 sized to enclose the proximal end 1216 of the mixing/dispensing chamber 1202. The inner circumference 1256 of the cover has complementary threads for mating with the threads 1218 on the brim 1214. The cover 1254 has a threaded opening 1258 for receiving the threaded rod 1242. The threaded opening 1258 is designed to mate with the threaded rod 1242. In a conventional manner the dispensing rod 1240 can be moved through the threaded opening 1258 by rotating the threaded rod 1242 in a clockwise direction relative to the threaded opening 1258 to move the threaded rod 1242 through the threaded opening 1258. Conversely, the threaded rod 1242 can be detached from the cover 1254 by rotating the threaded rod 1242 counterclockwise relative to the threaded opening 1258 to disengage the threads.

To operate the mixing/dispensing device 1200, all ingredients of the bone cement must be in the internal chamber 1208. Thereafter, the mixing rod assembly 1220 is attached to the mixing/dispensing chamber by mating the threads on the cover 1230 with the threads 1218 on the brim 1214 and screwing the cover 1230 and the brim 1214 together. Once the cover is attached, the ingredients are mixed by moving the rod 1221 back and forth in the internal chamber 1208 thus forcing the perforated mixing disc 1222 through the bone cement. The rod 1221 may also be rotated about its central axis to assist with the mixing process. When the mixing is completed, the cover 1230 is unscrewed from the brim 1214 and the mixing rod assembly 1220 is removed from the mixing/dispensing chamber and discarded.

The dispensing rod assembly 1240 is then attached to the mixing/dispensing chamber 1202 by mating the threads 1256 on the cover 1254 with the threads 1218 on the brim 1214 and screwing the cover 1254 and the brim 1214 together. Once the cover is attached, the mixed bone cement may be dispensed by rotating the handle 1252 to cause the threaded rod 1242 with the piston 1246 to move through the internal chamber 1208 in a screw like fashion. This motion causes the piston 1246 to move toward the distal end 1206 of the mixing/dispensing chamber 1202, forcing the bone cement through the opening 1210.

Preferably the interchangeable mixing and dispensing plunger is used with a prepackaged mixing/dispensing chamber, e.g. one in which the monomer and the polymer are preloaded into the internal chamber.

The mixing of the bone cement is an exothermic reaction, therefore, it may be desirable to cool the components and/or the mixing chamber to slowdown the reaction and subsequently extend the working time of the bone cement. Furthermore, if the reaction is slowed, the amount of time for dispensing of the bone cement will increase. In its simplest form, the components and/or the mixing chamber may be cooled by wrapping the mixing chamber with an ice pack, for example, a disposable instant ice pack. Alternatively, a more elaborate cooling system may be provided with the device for example, cold water could be circulated through the handle and/or the extension tubing to extend the working time.

Furthermore, it is desirable to ensure the bone cement is thoroughly mixed prior to using the compound is its designated application. After the dry and wet components are mixed either by shaking as described in conjunction with FIG. 3 or by means of mixing with a mixing rod, it may be of benefit to pass the mixed compound through a static mixer. The static mixer may be attached to an opening at a distal end of a delivery device. When configured this way, the bone cement is further mixed by passing the bone cement over a stationary object in the flow path that further mixes the compound as it passes over the object. A static mixer could be incorporated into an extension tube that connects the dispensing chamber to a site delivery device such as a cannula.

Although preferred embodiments of the invention are shown and described herein, it would be apparent to those skilled in the art that many changes and modifications may be made thereto without the departing from the scope of the invention, which is defined by the following claims.

What is claimed:

1. An apparatus for mixing and dispensing a multi-component compound to a cannula, comprising:
    a tubular body defining an internal chamber for mixing the multi-component compound therein, the tubular body having a distal end comprising an opening in communication with the internal chamber;
    a rod disposed within the tubular body, said rod having a proximal end extending out of the tubular body and a distal end extending into the tubular body;
    a moveable piston separate from and contained within the tubular body;
    a sensor for sensing a characteristic of the compound within the apparatus;
    an output valve having an inlet in fluid communication with said opening in said distal end of the tubular body, said output valve having a first outlet in fluid communication with a patient delivery lumen and a second outlet in fluid communication with a shunt lumen, said output valve configured to direct flow from the opening into either the patient delivery lumen or the shunt lumen, said output valve operably coupled to said sensor;
    a selectable locking mechanism carried by said rod, said locking mechanism having a first selectable configuration in which said locking mechanism allows said rod to move substantially freely relative to said piston and a second selectable configuration which couples said rod to said piston such that distal movement of said rod causes said piston to move distally through said tubular body.

2. The apparatus of claim 1, further comprising bone cement contained within said tubular body.

3. The apparatus of claim 1, further comprising a mixing disc near the distal end of the rod.

4. The apparatus of claim 3, wherein the removable cover is configured such that the moveable piston may be attached to the removable cover.

5. The apparatus of claim 3, further comprising a mechanism to attach the moveable piston to the mixing disc at the distal end of the rod.

6. The apparatus of claim 1, further comprising a mixing paddle near the distal end of the rod.

7. The apparatus of claim 1, wherein the proximal end of the tubular body is configured with a removable cover.

8. The apparatus of claim 1, wherein the moveable piston has a central opening through which the rod extends.

* * * * *